US007517965B2

(12) United States Patent
Koga et al.

(10) Patent No.: US 7,517,965 B2
(45) Date of Patent: Apr. 14, 2009

(54) NON-NEUTRALIZING ANTI-APC ANTIBODIES

(75) Inventors: Takaki Koga, Shizuoka (JP); Tsukasa Suzuki, Shizuoka (JP); Hiroyuki Saito, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 268 days.

(21) Appl. No.: 10/522,086

(22) PCT Filed: Jul. 17, 2003

(86) PCT No.: PCT/JP03/09087

§ 371 (c)(1),
(2), (4) Date: Oct. 5, 2005

(87) PCT Pub. No.: WO2004/009641

PCT Pub. Date: Jan. 29, 2004

(65) Prior Publication Data
US 2006/0121022 A1 Jun. 8, 2006

(30) Foreign Application Priority Data
Jul. 22, 2002 (JP) ............................. 2002-212582

(51) Int. Cl.
*C07K 16/00* (2006.01)
(52) U.S. Cl. .............................. 530/388.25; 530/387.3; 424/133.1; 424/135.1; 424/141.1; 424/145.1
(58) Field of Classification Search ....................... None
See application file for complete search history.

(56) References Cited

U.S. PATENT DOCUMENTS

| 4,208,479 | A | * | 6/1980 | Zuk et al. ................... 435/7.9 |
| 5,279,956 | A | | 1/1994 | Griffin et al. |
| 5,948,752 | A | | 9/1999 | Fujita et al. |
| 6,037,322 | A | * | 3/2000 | Grinnell et al. ................. 514/8 |
| 2006/0167230 | A1 | * | 7/2006 | Koga et al. ................ 530/387.3 |

FOREIGN PATENT DOCUMENTS

| EP | 0 138 222 | 4/1985 |
| EP | 0 287 028 | 10/1988 |
| EP | 1 222 929 | 7/2002 |
| JP | 2-236452 | 9/1990 |
| JP | 3-200066 | 9/1991 |
| JP | 11-124399 | 5/1999 |
| WO | WO 90/07524 | 7/1990 |
| WO | WO 93/09807 A1 | 5/1993 |
| WO | WO 95/34652 | 12/1995 |
| WO | 00-47626 | 8/2000 |

OTHER PUBLICATIONS

Suzuki et al., J. Biochem (Tokyo), 1985, 97:127-138.*
Strandberg et al., "Activated Protein C-Protein C Inhibitor Complex Formation: Characterization of a Neoepitope Provides Evidence for Extensive Insertion of the Reactive Center Loop," *Biochemistry*, 39:15713-15720 (2000).
Taylor et al., "Anticoagulant and Fibrinolytic Activities Are Promoted, Not Retarded, In Vivo After Thrombin Generation in the Presence of a Monoclonal Antibody That Inhibits Activation of Protein C," *Blood*, 79:1720-1728 (1992).
Ewert et al., "Stability improvement of antibodies for extracellular and intracellular applications: CDR grafting to stable frameworks and structure-based framework engineering," *Methods*, 34:184-199 (2004).
Griffin et al., "Activated Protein C: Potential Therapy for Severe Sepsis, Thrombosis, and Stroke," *Semin. Hematol.*, 39:197-205 (2002).
Gruber et al., "Inhibition of Thrombus Formation by Activated Recombinant Protein C in a Primate Model of Arterial Thrombosis," *Circulation*, 82:578-585 (1990).
Heeb et al., "Activation and Complexation of Protein C and Cleavage and Decrease of Protein S in Plasma of Patients With Intravascular Coagulation," *Blood*, 73:455-461 (1989).
Laurell et al., "Monoclonal Antibodies Against the Heparin-Dependent Protein C Inhibitor Suitable for Inhibitor Purification and Assay of Inhibitor Complexes," *Thromb. Haemost.*, 60:334-339 (1988).
Meijers et al., "Protein C inhibitor (plasminogen activator inhibitor-3) and the risk of venous thrombosis," *Br. J. Haematol.*, 118:604-609 (2002).
Cooper et al. "Intermolecular interactions between protein C inhibitor and coagulation proteases". Biochemistry 34:12991-12997, 1995.
Elisen et al. "Protein C inhibitor acts as a procoagulant by inhibiting the thrombomodulin-induced activation of protein C in human plasma". Blood 91(5):1542-1547, 1998.

(Continued)

Primary Examiner—Michael Szperka
(74) Attorney, Agent, or Firm—Fish & Richardson P.C.

(57) ABSTRACT

The present invention provides anti-aPC antibodies that suppress the inactivation of activated protein C (aPC), and uses thereof. The present inventors screened anti-aPC antibodies, and succeeded in isolating anti-aPC antibodies comprising the activity of suppressing aPC inactivation in blood. The antibodies of the present invention can be used to maintain aPC activity by suppressing aPC inactivation, and can thus be used to sustain aPC bioactivities, such as the activity of suppressing activation of the blood coagulation system, and anti-inflammatory activity. In addition, the present invention provides uses of the antibodies of the present invention in aPC therapy for diseases such as thrombosis and sepsis. The therapeutic effect of aPC can be prolonged in treatment that uses aPC administration by allowing an antibody of the present invention to bind with aPC. The antibodies of the present invention can be used in the treatment and prevention of diseases such as thrombosis and sepsis.

15 Claims, 1 Drawing Sheet

OTHER PUBLICATIONS

Meijers et al. "Identification of momclonal antibodies that inhibit the function of protein C inhibitor. Evidence for heparin-independent inhibition of activated protein C in plasma". Blood 74(2):1401-1403, 1988.

Strandberg et al. "A new method to measure plasma levels of activated protein C in complex with protein C inhibitor in patients with acute coronary syndromes". Blood Coagulation and Fibrinolysis 12(7):503-510, 2001.

Strandberg et al. "Complexes between activated protein C and protein C inhibitor measured with a new method". Thromb Haemost 86:1400-1408, 2001.

Suzuki. "Protein C inhibitor (PAI-3): structure and multi-function". Fibrinolysis & Proteolysis 14(273):133-145, 2000.

Suzuki et al. "Mechanism of inhibition of activated protein C by protein C inhibitor". J. Biochem 95:187-195, 1984.

Suzuki et al. "Protein C inhibitor", Journal of Biological Chemistry 258(1):163-168, 1983.

Suzuki et al. "Characterization of a cDNA for human protein C inhibitor". Journal of Biological Chemistry 262(2):611-616, 1987.

Taylor et al. "Protein C prevents the coagulopathic and lethal effects of *Escherichia coli* infusion in the baboon". J. Clin. Invest. 79:918-925, 1987.

Taylor et al. "DEGR-Factor Xa blocks disseminated intravascular coagulation initiated by *Escherichia coli* without preventing shock or organ damage". Blood 78(2):364-368, 1991.

Watanabe et al. "Plasma levels of activated protein C-protein C inhibitor complex in patients with hypercoagulable states". American Journal of Hematology 65:35-40, 2000.

Ware et al. "Localization of a factor VIII-inhibiting antibody epitope to a region between residues 338 and 363 of factor VIII heavy chain". Proc. Natl. Acad. Sci. USA 85(9):3165-3169, May 1988.

Bernard et al., "Efficacy and Safety of Recombinant Human Activated Protein C for Severe Sepsis," The New England Journal of Medicine, 344: 699-709 (2001).

Joyce et al. "Gene Expression Profile of Antithrombotic Protein C Defines New Mechanisms Modulating Inflammation and Apoptosis." The Journal of Biological Chemistry 276(14)11199-11203, Apr. 6, 2001.

Janeway et al., "The Interaction of the antibody molecule with specific antigen", Immunology, third edition, pp. 3:7-3:11 (1997).

Rudikoff et al., "Single amino substitution altering antigen-binding specificity" PNAS USA, vol. 79, pp. 1979-1983 (1982).

Kovari et al., "The use of antibody fragments for crystallization and structure determinations", Structure, vol. 3, pp. 1291-1293 (1995).

\* cited by examiner

VH REGION SEQUENCES OF ANTI-aPC ANTIBODIES

|  | CDR1 |  | CDR2 |
|---|---|---|---|
| aPC#79 | QVQLQQSGAELARPGASVKLSCKASGYTFT | DSYMN WVKQRTGQGLEWIG | EVYPETGNSYYNEKFKG |
| aPC#123 | QVQLQQSGPELVKPGASVKISCKASGYAFS | SSWMN WVKQRPGQGLEWIG | RIYPGDGDTNYNGKFRG |
| aPC#281 | QIQLVQSGPELEKPGETVRISCKASGYTFT | DYSLH WVKQAPGKGLKWMG | WINTETGEPTYADDLKG |
| aPC#285 | QVQLQQSGSEVVKPGASVKISCKASGYAFS | RSWMN WVKQRPGQGLEWIG | RIYPGDSIYNGKFKG |

| | | CDR3 | |
|---|---|---|---|
| aPC#79 | KATLTADRSSKTAYMQLNSLTSEDSAVYFCTR | GGTGFDY | WGQGTTLTVSSA (SEQ ID NO: 1) |
| aPC#123 | KATLTADKSSSTAYMQLTSLTSVDSAVYFCAR | WGITTAAWFAY | WGQGTLVTVSAA (SEQ ID NO: 2) |
| aPC#281 | RFAFSLETSATTAYLQINNLKNEDTATYFCAR | GITLDY | WGQGTSLTVSSA (SEQ ID NO: 3) |
| aPC#285 | KATLTADKSSTTAYMHLNSLTSVDSAVYFCAR | WGSSGSSWFAY | WGQGTLVTVSAA (SEQ ID NO: 4) |

VL REGION SEQUENCES OF ANTI-aPC ANTIBODIES

|  | CDR1 |  | CDR2 |
|---|---|---|---|
| aPC#79 | QIVLAQSPAIMSASLGERVTMTC | TASSSVSSSYLH WYQQKPGSSPKAWIY | STSNLASGAPT |
| aPC#123 | DIQMTQSPASLSASVGETVTITC | RTSENIYSYLA WYQQKQGKSPQLLVN | NAKTLAEGVPS |
| aPC#281 | DNVMSQSPSSLAVSVGEKVTMSC | KSSQSLLSSSNQKNFLA WYQQKPGQSPKLLI | SWASTRHSGVPD |
| aPC#285 | DIQMTQSPASLSASMGETVTITC | RTSENIYSYLA WYRQKQGKSPQLLVY | NAKTLAEGVPS |

| | | CDR3 | |
|---|---|---|---|
| aPC#79 | RFSGSGSGTSYSLTISSMEAEDAATYYCHQ | YHRSPFT | FGSGTKLEIK (SEQ ID NO: 5) |
| aPC#123 | RFSGSGSGTQFSLKINSLQPEDFGTYYCQH | YYGTPPT | FGGGTKLEIK (SEQ ID NO: 6) |
| aPC#281 | RFTGSGSGTDFTLTISSVNAEDLAVYYCQQ | YYRYPLT | FGAGTKLELK (SEQ ID NO: 7) |
| aPC#285 | RFSGSGSGTQFSLRINSLQPEDFGSYFCQH | YYGSPYT | FGGGTKLEIK (SEQ ID NO: 8) |

FIG. 1

SEQUENCE LISTING

<160> NUMBER OF SEQ ID NOS: 34

<210> SEQ ID NO 1
<211> LENGTH: 117
<212> TYPE: PRT
<213> ORGANISM: Mus musculus

<400> SEQUENCE: 1

```
Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Asp Ser
            20                  25                  30

Tyr Met Asn Trp Val Lys Gln Arg Thr Gly Gln Gly Leu Glu Trp Ile
        35                  40                  45

Gly Glu Val Tyr Pro Glu Thr Gly Asn Ser Tyr Tyr Asn Glu Lys Phe
    50                  55                  60

Lys Gly Lys Ala Thr Leu Thr Ala Asp Arg Ser Ser Lys Thr Ala Tyr
65                  70                  75                  80

Met Gln Leu Asn Ser Leu Thr Ser Glu Asp Ser Ala Val Tyr Phe Cys
                85                  90                  95

Thr Arg Gly Gly Thr Gly Phe Asp Tyr Trp Gly Gln Gly Thr Thr Leu
            100                 105                 110

Thr Val Ser Ser Ala
        115
```

<210> SEQ ID NO 2
<211> LENGTH: 121
<212> TYPE: PRT
<213> ORGANISM: Mus musculus

<400> SEQUENCE: 2

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Thr Asn Tyr Asn Gly Lys Phe
    50                  55                  60

Arg Gly Lys Ala Thr Leu Thr Ala Asp Lys Ser Ser Ser Thr Ala Tyr
65                  70                  75                  80

Met Gln Leu Thr Ser Leu Thr Ser Val Asp Ser Ala Val Tyr Phe Cys
                85                  90                  95

Ala Arg Trp Gly Ile Thr Thr Ala Ala Trp Phe Ala Tyr Trp Gly Gln
            100                 105                 110

Gly Thr Leu Val Thr Val Ser Ala Ala
        115                 120
```

<210> SEQ ID NO 3
<211> LENGTH: 116
<212> TYPE: PRT
<213> ORGANISM: Mus musculus

<400> SEQUENCE: 3

```
Gln Ile Gln Leu Val Gln Ser Gly Pro Glu Leu Glu Lys Pro Gly Glu
1               5                   10                  15

Thr Val Arg Ile Ser Cys Lys Ala Ser Gly Tyr Thr Phe Thr Asp Tyr
            20                  25                  30

Ser Leu His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Leu
    50                  55                  60

Lys Gly Arg Phe Ala Phe Ser Leu Glu Thr Ser Ala Thr Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Ile Thr Leu Asp Tyr Trp Gly Gln Gly Thr Ser Leu Thr
            100                 105                 110

Val Ser Ser Ala
        115
```

<210> SEQ ID NO 4
<211> LENGTH: 121
<212> TYPE: PRT
<213> ORGANISM: Mus musculus

<400> SEQUENCE: 4

```
Gln Val Gln Leu Gln Gln Ser Gly Ser Glu Val Val Lys Pro Gly Ala
1               5                   10                  15

Ser Val Lys Ile Ser Cys Lys Ala Ser Gly Tyr Ala Phe Ser Arg Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Ser Ile Tyr Asn Gly Lys Phe
    50                  55                  60

Lys Gly Lys Ala Thr Leu Thr Ala Asp Lys Ser Ser Ser Thr Ala Tyr
65                  70                  75                  80
```

-continued

```
Met His Leu Asn Ser Leu Thr Ser Val Asp Ser Ala Val Tyr Phe Cys
                85                  90                  95

Ala Arg Trp Gly Ser Gly Ser Ser Trp Phe Ala Tyr Trp Gly Gln
            100                 105                 110

Gly Thr Leu Val Thr Val Ser Ala Ala
        115                 120
```

<210> SEQ ID NO 5
<211> LENGTH: 108
<212> TYPE: PRT
<213> ORGANISM: Mus musculus

<400> SEQUENCE: 5

```
Gln Ile Val Leu Ala Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Ala Trp
        35                  40                  45

Ile Tyr Ser Thr Ser Asn Leu Ala Ser Gly Ala Pro Thr Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Phe Thr Phe Gly Ser Gly Thr Lys Leu Glu Ile Lys
            100                 105
```

<210> SEQ ID NO 6
<211> LENGTH: 107
<212> TYPE: PRT
<213> ORGANISM: Mus musculus

<400> SEQUENCE: 6

```
Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Asn Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Thr Tyr Tyr Cys Gln His Tyr Tyr Gly Thr Pro Pro
                85                  90                  95

Thr Phe Gly Gly Gly Thr Lys Leu Glu Ile Lys
            100                 105
```

<210> SEQ ID NO 7
<211> LENGTH: 113
<212> TYPE: PRT
<213> ORGANISM: Mus musculus

<400> SEQUENCE: 7

```
Asp Asn Val Met Ser Gln Ser Pro Ser Ser Leu Ala Val Ser Val Gly
1               5                   10                  15
```

Glu Lys Val Thr Met Ser Cys Lys Ser Ser Gln Ser Leu Leu Ser Ser
            20                  25                  30

Ser Asn Gln Lys Asn Phe Leu Ala Trp Tyr Gln Gln Lys Pro Gly Gln
                35                  40                  45

Ser Pro Lys Leu Leu Ile Ser Trp Ala Ser Thr Arg His Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Asn Ala Glu Asp Leu Ala Val Tyr Tyr Cys Gln Gln
                85                  90                  95

Tyr Tyr Arg Tyr Pro Leu Thr Phe Gly Ala Gly Thr Lys Leu Glu Leu
            100                 105                 110

Lys

<210> SEQ ID NO 8
<211> LENGTH: 107
<212> TYPE: PRT
<213> ORGANISM: Mus musculus

<400> SEQUENCE: 8

Asp Ile Gln Met Thr Gln Ser Pro Ala Ser Leu Ser Ala Ser Met Gly
1               5                   10                  15

Glu Thr Val Thr Ile Thr Cys Arg Thr Ser Glu Asn Ile Tyr Ser Tyr
            20                  25                  30

Leu Ala Trp Tyr Arg Gln Lys Gln Gly Lys Ser Pro Gln Leu Leu Val
                35                  40                  45

Tyr Asn Ala Lys Thr Leu Ala Glu Gly Val Pro Ser Arg Phe Ser Gly
        50                  55                  60

Ser Gly Ser Gly Thr Gln Phe Ser Leu Arg Ile Asn Ser Leu Gln Pro
65                  70                  75                  80

Glu Asp Phe Gly Ser Tyr Phe Cys Gln His Tyr Tyr Gly Ser Pro Tyr
                85                  90                  95

Thr Phe Gly Gly Gly Thr Lys Leu Glu Ile Lys
            100                 105

<210> SEQ ID NO 9
<211> LENGTH: 5
<212> TYPE: PRT
<213> ORGANISM: Mus musculus

<400> SEQUENCE: 9

Asp Ser Tyr Met Asn
1               5

<210> SEQ ID NO 10
<211> LENGTH: 17
<212> TYPE: PRT
<213> ORGANISM: Mus musculus

<400> SEQUENCE: 10

Glu Val Tyr Pro Glu Thr Gly Asn Ser Tyr Tyr Asn Glu Lys Phe Lys
1               5                   10                  15

Gly

<210> SEQ ID NO 11
<211> LENGTH: 7
<212> TYPE: PRT
<213> ORGANISM: Mus musculus

```
<400> SEQUENCE: 11

Gly Gly Thr Gly Phe Asp Tyr
1               5

<210> SEQ ID NO 12
<211> LENGTH: 5
<212> TYPE: PRT
<213> ORGANISM: Mus musculus

<400> SEQUENCE: 12

Ser Ser Trp Met Asn
1               5

<210> SEQ ID NO 13
<211> LENGTH: 17
<212> TYPE: PRT
<213> ORGANISM: Mus musculus

<400> SEQUENCE: 13

Arg Ile Tyr Pro Gly Asp Gly Asp Thr Asn Tyr Asn Gly Lys Phe Arg
1               5                   10                  15

Gly

<210> SEQ ID NO 14
<211> LENGTH: 11
<212> TYPE: PRT
<213> ORGANISM: Mus musculus

<400> SEQUENCE: 14

Trp Gly Ile Thr Thr Ala Ala Trp Phe Ala Tyr
1               5                   10

<210> SEQ ID NO 15
<211> LENGTH: 5
<212> TYPE: PRT
<213> ORGANISM: Mus musculus

<400> SEQUENCE: 15

Asp Tyr Ser Leu His
1               5

<210> SEQ ID NO 16
<211> LENGTH: 17
<212> TYPE: PRT
<213> ORGANISM: Mus musculus

<400> SEQUENCE: 16

Trp Ile Asn Thr Glu Thr Gly Glu Pro Thr Tyr Ala Asp Asp Leu Lys
1               5                   10                  15

Gly

<210> SEQ ID NO 17
<211> LENGTH: 6
<212> TYPE: PRT
<213> ORGANISM: Mus musculus

<400> SEQUENCE: 17

Gly Ile Thr Leu Asp Tyr
1               5

<210> SEQ ID NO 18
<211> LENGTH: 5
<212> TYPE: PRT
```

```
<213> ORGANISM: Mus musculus

<400> SEQUENCE: 18

Arg Ser Trp Met Asn
1               5

<210> SEQ ID NO 19
<211> LENGTH: 17
<212> TYPE: PRT
<213> ORGANISM: Mus musculus

<400> SEQUENCE: 19

Arg Ile Tyr Pro Gly Asp Gly Asp Ser Ile Tyr Asn Gly Lys Phe Lys
1               5                   10                  15

Gly

<210> SEQ ID NO 20
<211> LENGTH: 11
<212> TYPE: PRT
<213> ORGANISM: Mus musculus

<400> SEQUENCE: 20

Trp Gly Ser Ser Gly Ser Ser Trp Phe Ala Tyr
1               5                   10

<210> SEQ ID NO 21
<211> LENGTH: 12
<212> TYPE: PRT
<213> ORGANISM: Mus musculus

<400> SEQUENCE: 21

Thr Ala Ser Ser Ser Val Ser Ser Ser Tyr Leu His
1               5                   10

<210> SEQ ID NO 22
<211> LENGTH: 11
<212> TYPE: PRT
<213> ORGANISM: Mus musculus

<400> SEQUENCE: 22

Ser Thr Ser Asn Leu Ala Ser Gly Ala Pro Thr
1               5                   10

<210> SEQ ID NO 23
<211> LENGTH: 7
<212> TYPE: PRT
<213> ORGANISM: Mus musculus

<400> SEQUENCE: 23

Tyr His Arg Ser Pro Phe Thr
1               5

<210> SEQ ID NO 24
<211> LENGTH: 11
<212> TYPE: PRT
<213> ORGANISM: Mus musculus

<400> SEQUENCE: 24

Arg Thr Ser Glu Asn Ile Tyr Ser Tyr Leu Ala
1               5                   10

<210> SEQ ID NO 25
<211> LENGTH: 11
<212> TYPE: PRT
```

<213> ORGANISM: Mus musculus

<400> SEQUENCE: 25

Asn Ala Lys Thr Leu Ala Glu Gly Val Pro Ser
1               5                   10

<210> SEQ ID NO 26
<211> LENGTH: 7
<212> TYPE: PRT
<213> ORGANISM: Mus musculus

<400> SEQUENCE: 26

Tyr Tyr Gly Thr Pro Pro Thr
1               5

<210> SEQ ID NO 27
<211> LENGTH: 17
<212> TYPE: PRT
<213> ORGANISM: Mus musculus

<400> SEQUENCE: 27

Lys Ser Ser Gln Ser Leu Leu Ser Ser Ser Asn Gln Lys Asn Phe Leu
1               5                   10                  15

Ala

<210> SEQ ID NO 28
<211> LENGTH: 12
<212> TYPE: PRT
<213> ORGANISM: Mus musculus

<400> SEQUENCE: 28

Ser Trp Ala Ser Thr Arg His Ser Gly Val Pro Asp
1               5                   10

<210> SEQ ID NO 29
<211> LENGTH: 7
<212> TYPE: PRT
<213> ORGANISM: Mus musculus

<400> SEQUENCE: 29

Tyr Tyr Arg Tyr Pro Leu Thr
1               5

<210> SEQ ID NO 30
<211> LENGTH: 7
<212> TYPE: PRT
<213> ORGANISM: Mus musculus

<400> SEQUENCE: 30

Tyr Tyr Gly Ser Pro Tyr Thr
1               5

<210> SEQ ID NO 31
<211> LENGTH: 5
<212> TYPE: PRT
<213> ORGANISM: Artificial
<220> FEATURE:
<223> OTHER INFORMATION: heavy chain CDR1
<220> FEATURE:
<221> NAME/KEY: MISC_FEATURE
<222> LOCATION: (1)..(1)
<223> OTHER INFORMATION: "Xaa" at location 1 stands for Ser or Arg

<400> SEQUENCE: 31

Xaa Ser Trp Met Asn

-continued

<210> SEQ ID NO 32
<211> LENGTH: 17
<212> TYPE: PRT
<213> ORGANISM: Artificial
<220> FEATURE:
<223> OTHER INFORMATION: heavy chain CDR2
<220> FEATURE:
<221> NAME/KEY: MISC_FEATURE
<222> LOCATION: (9)..(9)
<223> OTHER INFORMATION: "Xaa" at location 9 stands for Thr or Ser
<220> FEATURE:
<221> NAME/KEY: MISC_FEATURE
<222> LOCATION: (10)..(10)
<223> OTHER INFORMATION: "Xaa" at location 10 stands for Asn or Ile
<220> FEATURE:
<221> NAME/KEY: MISC_FEATURE
<222> LOCATION: (16)..(16)
<223> OTHER INFORMATION: "Xaa" at location 16 stands for Arg or Lys

<400> SEQUENCE: 32

Arg Ile Tyr Pro Gly Asp Gly Asp Xaa Xaa Tyr Asn Gly Lys Phe Xaa
1               5                   10                  15

Gly

<210> SEQ ID NO 33
<211> LENGTH: 11
<212> TYPE: PRT
<213> ORGANISM: Artificial
<220> FEATURE:
<223> OTHER INFORMATION: heavy chain CDR3
<220> FEATURE:
<221> NAME/KEY: MISC_FEATURE
<222> LOCATION: (3)..(3)
<223> OTHER INFORMATION: "Xaa" at location 3 stands for Ile or Ser
<220> FEATURE:
<221> NAME/KEY: MISC_FEATURE
<222> LOCATION: (4)..(4)
<223> OTHER INFORMATION: "Xaa" at location 4 stands for Thr or Ser
<220> FEATURE:
<221> NAME/KEY: MISC_FEATURE
<222> LOCATION: (5)..(5)
<223> OTHER INFORMATION: "Xaa" at location 5 stands for Thr or Gly
<220> FEATURE:
<221> NAME/KEY: MISC_FEATURE
<222> LOCATION: (6)..(6)
<223> OTHER INFORMATION: "Xaa" at location 6 stands for Ala or Ser
<220> FEATURE:
<221> NAME/KEY: MISC_FEATURE
<222> LOCATION: (7)..(7)
<223> OTHER INFORMATION: "Xaa" at location 7 stands for Ala or Ser

<400> SEQUENCE: 33

Trp Gly Xaa Xaa Xaa Xaa Xaa Trp Phe Ala Tyr
1               5                   10

<210> SEQ ID NO 34
<211> LENGTH: 7
<212> TYPE: PRT
<213> ORGANISM: Artificial
<220> FEATURE:
<223> OTHER INFORMATION: light chain CDR3
<220> FEATURE:
<221> NAME/KEY: MISC_FEATURE
<222> LOCATION: (4)..(4)
<223> OTHER INFORMATION: "Xaa" at location 4 stands for Thr or Ser
<220> FEATURE:
<221> NAME/KEY: MISC_FEATURE -continued

```
<222> LOCATION: (6)..(6)
<223> OTHER INFORMATION: "Xaa" at location 6 stands for Pro or Tyr

<400> SEQUENCE: 34

Tyr Tyr Gly Xaa Pro Xaa Thr
1               5
```

NON-NEUTRALIZING ANTI-APC ANTIBODIES

CROSS-REFERENCE TO RELATED APPLICATIONS

This application is the National Stage of International Application No. PCT/JP2003/009087, filed Jul. 17, 2003, which claims the benefit of Japanese Patent Application Ser. No. 2002-212582, filed on Jul. 22, 2002. The contents of both applications are hereby incorporated by reference in their entireties.

TECHNICAL FIELD

The present invention relates to non-neutralizing antibodies against activated protein C.

BACKGROUND ART

Venous thrombosis frequently occurs after major abdominal surgery or leg joint arthroplasty. Currently, therapy is mainly preventive, using low-molecular-weight heparin and warfarin. However, treatment with low-molecular-weight heparin requires subcutaneous administration every day. Warfarin is given orally, but has an exceedingly high protein-binding rate, and this interactivity limits its combined use with other drugs. In addition, both drugs tend to cause bleeding. Thus, if there is an anti-thrombotic agent that is effective over a longer duration, and that does not produce hemorrhagic tendencies, its administration immediately after operation and just prior to discharge from the hospital can prevent thrombosis and improve quality of life (QOL) for patients. The development of anti-thrombotic agents, particularly those effective over longer durations, is also anticipated for other types of thromboses.

A thrombus is formed by the activation of platelets and the blood coagulation system. It is believed that platelets chiefly contribute to the formation of arterial thrombus, while the coagulation system mainly contributes to the formation of venous thrombus. Activation of the blood coagulation system brings about thrombin formation, which leads to the production of fibrin, a major factor in the thrombus network. Meanwhile, thrombin alters its own properties upon binding to thrombomodulin on the surface of vascular endothelia, thus activating protein C (PC). The activated PC (aPC) uses protein S as a coenzyme to inactivate Factors Va and VIIIa, thereby suppressing the coagulation system. Furthermore, aPC comprises the activity of suppressing fibrinolysis-inhibiting substances, such as PAI-1 (Plasminogen Activator Inhibitor-1) and TAFI (Thrombin Activatable Fibrinolysis Inhibitor), and thus enhances the fibrinolysis system. PC and aPC are thus presumed to play important roles in a negative feedback mechanism for the activated blood coagulation system. Indeed, both congenital PC deficiency and aPC resistance due to Factor Va mutations can be causative factors in thrombosis, and thus aPC is expected to be effective in treating and preventing thrombosis.

Although there was no effective drug to treat sepsis, a recent study reported that recombinant aPC was effective in treating sepsis (N. Engl. J. Med. 2001, 344: 699-709). aPC has also been suggested to act on vascular endothelia and to comprise anti-inflammatory activity (J. Biol. Chem. 2001, 276: 11199-11203). In addition, the anti-inflammatory action in a sepsis model is reported to be based on an activity other than the suppression of thrombin production (J. Clin. Invest. 1987, 79: 918-25).

The half-life of aPC in blood is very short (only 20 to 30 minutes), requiring its continuous intravenous administration or long-term repetitive administration. The reason for this short half-life is that aPC is irreversibly inactivated by physiological inhibitors in the body, such as protein C inhibitor (PCI) or α1-antitrypsin (AAT). Even if PC, the precursor of aPC, is used in preparations, its half-life in vivo is as short as six to eight hours. Therefore, such preparations should be administered continuously or frequently, which is inefficient from the viewpoint of healthcare economics.

DISCLOSURE OF THE INVENTION

As described above, aPC functions to feedback on the blood coagulation system, and aPC generation and action are constrained to local regions where the coagulation system has been activated. Accordingly, when systemically administered, aPC must be given continuously at high doses to deliver it to the local regions where aPC is needed, and to compensate for its consumption, caused by inactivation. An efficient agent could potentiate the activity of aPC produced locally and endogenously. The action of such an agent would be limited to the local region, and prolonged even when given as a single low dose administration, because the agent itself is usually not consumed. In this context, the present inventors developed an agent which can potentiate the action of endogenous aPC by suppressing aPC inactivation and extending aPC half-life.

To this end, the present inventors cloned hybridomas that produced monoclonal antibodies against aPC. The inventors screened the hybridomas on a large scale for antibodies suppressing aPC inactivation in blood, and succeeded in isolating anti-aPC antibodies that strongly suppressed aPC inactivation. These antibodies were also confirmed to suppress aPC inactivation caused by PCI. The antibodies of the present invention suppress the action of the blood coagulation system by suppressing aPC inactivation, and thus are highly useful in treating and preventing thrombosis. The antibodies of the present invention can also be used in combination with aPC, or used alone as therapeutic agents for sepsis or such to potentiate aPC activity by suppressing aPC inactivation in blood.

Specifically, the present invention relates to anti-aPC antibodies that suppress aPC inactivation, and uses thereof. More specifically, the present invention relates to:

(1) an antibody against protein C or activated protein C (aPC), comprising the activity of potentiating an activity of activated protein C in vivo;

(2) an antibody against protein C or activated protein C, comprising the activity of suppressing the inactivation of activated protein C in vivo;

(3) an antibody against protein C or activated protein C, comprising the activity of suppressing: (a) the inactivation of activated protein C caused by blood or (b) the inactivation of activated protein C caused by a physiological inhibitor of activated protein C, or both (a) and (b);

(4) the antibody of (3), wherein the physiological inhibitor of activated protein C is a serine protease inhibitor (SERPIN);

(5) the antibody of (4), wherein the serine protease inhibitor (SERPIN) is a protein C inhibitor or α1-antitrypsin;

(6) the antibody of any one of (1) to (3), comprising a complementarity-determining region comprising any one of the amino acid sequences of (a) to (f), or a complementarity-determining region functionally equivalent thereto:

(a) the amino acid sequences of SEQ ID NOs: 9, 10, and 11;
(b) the amino acid sequences of SEQ ID NOs: 21, 22, and 23;
(c) the amino acid sequences of SEQ ID NOs: 31, 32, and 33;

(d) the amino acid sequences of SEQ ID NOs: 24, 25, and 34;
(e) the amino acid sequences of SEQ ID NOs: 15, 16, and 17; and
(f) the amino acid sequences of SEQ ID NOs: 27, 28, and 29;
(7) the antibody of any one of (1) to (3), wherein the antibody is selected from the group consisting of a human antibody, humanized antibody, chimeric antibody, antibody fragment, single-chain antibody, and diabody;
(8) a composition comprising the antibody of any one of (1) to (3), and a pharmaceutically acceptable carrier;
(9) the composition of (8), further comprising protein C and/or activated protein C;
(10) the composition of (8) or (9), wherein the composition is a pharmaceutical composition that can be used to prevent or treat a disease which is developed and/or advanced upon a decrease or loss of an activity of activated protein C;
(11) the composition of (10), wherein the disease is developed upon the enhancement of the blood coagulation reaction and/or inflammatory reaction;
(12) the composition of (11), wherein the disease developed upon the enhancement of the blood coagulation reaction and/or inflammatory reaction is selected from the group consisting of sepsis, disseminated intravascular coagulation syndrome, arterial thrombosis, and venous thrombosis;
(13) a method for producing protein C or activated protein C whose inactivation has been suppressed, comprising the step of contacting the antibody of any one of (1) to (3) with protein C or activated protein C;
(14) a method for preventing or treating a disease developed and/or advanced upon a decrease or loss of an activity of activated protein C, comprising the step of administering: (a) protein C and/or activated protein C, and (b) the antibody of any one of (1) to (3); and
(15) a kit for preventing or treating a disease developed and/or advanced upon a decrease or loss of an activity of activated protein C, wherein the kit comprises (a) at least one selected from the group consisting of protein C, activated protein C, and an antibody of any one of (1) to (3), and (b) a recording medium comprising a description about a combined use of the antibody with protein C and/or activated protein C in a therapeutically effective amount, or a link to the description.

The present invention provides non-neutralizing anti-aPC antibodies that suppress aPC inactivation and extend its half-life. The present inventors discovered that among the non-neutralizing antibodies against aPC existed antibodies that could potentiate the anticoagulant activity of aPC by preventing it from being inactivated by PCI or AAT in blood, thus extending aPC's in vivo life. Herein, the term "aPC inactivation" refers to a decrease or loss in aPC's biological activity. Specifically, the term "aPC inactivation" refers to irreversible inactivation of aPC by blood or by an in vivo physiological inhibitor, such as PCI and AAT. Specifically, the term "aPC inactivation" refers to the inactivation of, for example, aPC's anticoagulant activity. aPC can be inactivated, for example, by incubating it in blood plasma. aPC can also be inactivated by contacting it with an in vivo inhibitory substance, such as PCI and AAT. The antibodies of the present invention are those that suppress aPC inactivation by blood plasma and/or by a physiological aPC inhibitor (for example, PCI). An antibody of the present invention can be used to suppress aPC inactivation in vivo, and to potentiate the in vivo activity of activated protein C relative to that in the absence of the antibody. The suppression of aPC inactivation by an antibody can be measured by a method described in the Examples, or by an alternative method. Specifically, for example, aPC is incubated with a test antibody, and at the same time, or after this incubation, it is further incubated with blood plasma or an aPC inhibitor, such as PCI, and aPC activity is then determined. An antibody which decreases the degree of aPC inactivation as compared to a control, in which aPC is incubated with blood plasma or the aPC inhibitor but not with the antibody, is considered to comprise the activity of suppressing aPC inactivation. aPC activity includes anticoagulant activity, which can be quantified, for example, by using a known method to measure APTT (activated partial thromboplastin time). Alternatively, aPC activity can be assayed using a low-molecular-weight compound, such as the chromogenic substrate pyroGlu-Pro-Arg-pNA.HCl (S-2366).

Physiological aPC inhibitors include, for example, serine protease inhibitors (SERPINs), and specific examples of such inhibitors include protein C inhibitor (PCI, Suzuki, K. et al., J. Biol. Chem., 258, 163-168, 1983; Suzuki, K., Fibrinolysis Proteolysis, 14, 133-145, 2000; Suzuki, K. et al., J. Biol. Chem., 262, 611-616, 1987; Zechmeister-Machhart, M. et al., Gene, 186, 61-66, 1997; Wakita, T. et al., FEBS Lett., 429, 263-268, 1998; Yuasa, J. et al., Thromb. Haemost. 83, 262-267, 2000) and α1-antitrypsin (AAT, Heeb, M. J. and Griffin, J. H., J. Biol. Chem., 263, 11613-11616, 1988).

The present invention also provides antibodies against aPC, which can be prepared by the steps of:
i) determining the inactivation by blood of aPC that is free of or bound to an anti-aPC antibody; and
ii) selecting an antibody which suppresses the inactivation of aPC when bound to it, compared to aPC not bound to that antibody.

The present invention also provides antibodies against aPC, which can be prepared by the steps of:
i) determining the inactivation by an aPC inactivator of aPC that is free of or bound to an anti-aPC antibody; and
ii) selecting an antibody which suppresses the inactivation of aPC when bound to it, compared to aPC not bound to that antibody.

The blood may be whole blood or plasma. The aPC inactivator includes physiological aPC inhibitors, for example, PCI and AAT. An antibody against aPC is bound to aPC by contacting the two in a solution, for example, by incubating a solution comprising the two for five minutes to several hours (for example, for about one hour). aPC can be inactivated by blood or an aPC inactivator by, for example, contacting aPC with blood or the aPC inhibitor; for example, by incubating a solution containing the two for five minutes to several hours (for example, for about one hour).

The anti-aPC antibodies of the present invention may be monoclonal antibodies (including full-length monoclonal antibodies), polyclonal antibodies, or mutant antibodies derived from these antibodies. Monoclonal antibodies are preferable because they are homogeneous and stably produced.

Herein, "monoclonal antibody" refers to an antibody obtained from a group of substantially homogeneous antibodies, that is, an antibody group wherein the antibodies constituting the group are homogeneous except for naturally occurring mutants that exist in a small amount. Monoclonal antibodies are highly specific and interact with a single antigenic site. Furthermore, each monoclonal antibody targets a single antigenic determinant (epitope) on an antigen, as compared to common polyclonal antibody preparations that typically contain various antibodies against diverse antigenic determinants. In addition to their specificity, monoclonal antibodies are advantageous in that they are produced from hybridoma cultures not contaminated with other immunoglobulins. The qualifier "monoclonal" indicates a characteristic of antibodies obtained from a substantially homogeneous group of antibodies, and does not specify antibodies produced by a particular method. For example, a monoclonal antibody to be used in the present invention can be produced by, for example, hybridoma methods (Kohler and Milstein, Nature 256:495, 1975) or recombination methods (U.S. Pat. No. 4,816,567). The monoclonal antibodies used in the present invention can be also isolated from a phage antibody library (Clackson et al., Nature 352:624-628, 1991; Marks et al., J. Mol. Biol. 222:581-597, 1991). The monoclonal antibodies of the present invention particularly comprise "chimeric" antibodies (immunoglobulins), wherein a part of a heavy (H) chain and/or light (L) chain is derived from a specific species or a specific antibody class or subclass, and the remaining portion of the chain is derived from another species, or another antibody class or subclass. Furthermore, mutant antibodies and antibody fragments thereof are also comprised in the present invention (U.S. Pat. No. 4,816,567; Morrison et al., Proc. Natl. Acad. Sci. USA 81:6851-6855, 1984).

Herein, "mutant antibody" refers to an antibody comprising a variant amino acid sequence in which one or more amino acid residues have been altered. For example, the variable region of an antibody can be modified to improve its biological properties, such as antigen binding. Such modifications can be achieved by site-directed mutagenesis (see Kunkel, Proc. Natl. Acad. Sci. USA 82: 488 (1985)), PCR-based mutagenesis, cassette mutagenesis, and the like. Such mutants comprise an amino acid sequence which is at least 70% identical to the amino acid sequence of a heavy or light chain variable region of the antibody, more preferably at least 75%, even more preferably at least 80%, still more preferably at least 85%, yet more preferably at least 90%, and most preferably at least 95% identical. Herein, sequence identity is defined as the percentage of residues identical to those in the antibody's original amino acid sequence, determined after the sequences are aligned and gaps are appropriately introduced to maximize the sequence identity as necessary.

Specifically, the identity of one nucleotide sequence or amino acid sequence to another can be determined using the algorithm BLAST, by Karlin and Altschul (Proc. Natl. Acad. Sci. USA, 90: 5873-5877, 1993). Programs such as BLASTN and BLASTX were developed based on this algorithm (Altschul et al., J. Mol. Biol. 215: 403-410, 1990). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST); http://www.ncbi.nlm.nih.gov)

Polyclonal and monoclonal antibodies can be prepared by methods known to those skilled in the art. For example, the antibodies can be prepared by the methods described below.

aPC to be used for the immunization of animals includes the full-length aPC, comprising its entire amino acid sequence, or its partial peptides, which are prepared by recombinant DNA techniques or chemical synthesis. The amino acid sequences of the aPCs of humans and other mammals are known (Mather, T. et al., EMBO J. 15:6822-6831 (1996); Foster, D.C., Proc. Natl. Acad. Sci. 82:4673-4677 (1985)). For example, commercially available aPC (protein C from human plasma, activated, SIGMA, #P2200) can be used as the antigen. As the antigen for immunization, aPC itself, or its partial peptides, can be used without modification, or after being conjugated with a carrier protein. When a carrier protein is used, for example, the antigen aPC is first coupled with the carrier protein (for example, thyroglobulin), and then an adjuvant is added thereto. Such adjuvants include Freund's complete and incomplete adjuvants and the like, any of which can be combined together.

An antigen prepared as described above is given to a mammal, such as a mouse, rat, hamster, guinea pig, horse, monkey, rabbit, goat, and sheep. This immunization can be performed by any existing method, including typically used intravenous injections, subcutaneous injections, and intraperitoneal injections. There are no restrictions as to the immunization intervals. Immunization may be carried out at intervals of several days to several weeks, preferably four to 21 days. A mouse can be immunized, for example, at a single dose of 10 to 100 µg (for example, 20 to 40 µg) of the antigen protein, but the dose is not limited to these values.

Before the first immunization, and three to seven days after the second and subsequent immunizations, blood is collected from the animals, and the sera are analyzed for antibody titer. To promote an immune response, an aggregating agent such as alum is preferably used. In general, selected mammalian antibodies have sufficiently high antigen binding affinity. Antibody affinity can be determined using a saturation binding assay, an enzyme-linked immunosorbent assay (ELISA), or a competitive assay (for example, radioimmunoassay).

Polyclonal antibodies can be screened by a conventional crosslinking analysis, such as that described in "Antibodies, A Laboratory Manual (Cold Spring Harbor Laboratories, Harlow and David Lane edit. (1988))". An alternative method is, for example, epitope mapping (Champe et al., J. Biol. Chem. 270:1388-1394 (1995)). A preferred method for determining polypeptide or antibody titers comprises quantifying antibody-binding affinity. In other embodiments, methods for assessing one or more biological properties of an antibody are also used in addition to or instead of the methods for determining antibody-binding affinity. Such analytical methods are particularly useful because they demonstrate the therapeutic effectiveness of antibodies. When an antibody exhibits an improved property in such analysis, its binding affinity is generally, but not always, enhanced.

Hybridomas which are used to prepare monoclonal antibodies can be obtained, for example, by the method of Milstein et al. (Kohler, G., and Milstein, C., Methods Enzymol. 1981, 73, 3-46). Myeloma cells to be fused with antibody-producing cells may be cell lines derived from any of the various animals, such as mice, rats, and humans, which are generally available to those skilled in the art. The cell lines to be used are drug-resistant, and cannot survive in a selective medium (e.g., HAT medium) in an unfused state, but can survive in a fused state. 8-azaguanine-resistant cell lines are generally used, which are deficient in hypoxanthine-guanine-phosphoribosyl transferase and cannot grow in a hypoxanthine-aminopterin-thymidine (HAT) medium. Preferred myeloma cells include a variety of known cell lines, for example, P3x63Ag8.653 (J. Immunol. (1979) 123: 1548-1550), P3x63Ag8U.1 (Current Topics in Microbiology and Immunology (1978) 81: 1-7), NS-1 (Kohler, G. and Milstein, C., Eur. J. Immunol. (1976) 6: 511-519), MPC-11 (Margulies, D. H. et al., Cell (1976) 8: 405-415), SP2/0 (Shulman, M. et al., Nature (1978) 276: 269-270), F0 (de St. Groth, S. F. et al., J. Immunol. Methods (1980) 35: 1-21), S194 (Trowbridge, I. S., J. Exp. Med. (1978) 148: 313-323), R210 (Galfre, G. et al., Nature (1979) 277: 131-133), and P3U1 (J. Exp. Med. 1979, 150:580; Curr Top Microbiol. Immunol. 1978, 81:1). Human myeloma and mouse-human heteromycloma cell lines can also be used to produce human monoclonal antibodies (Kozbar, J. Immunol. 133:3001 (1984); Brodeur et al., Monoclonal Antibody Production Techniques and Application, pp. 51-63 (Marcel Dekker, Inc., New York, 1987)). Antibody-producing cells are collected, for example, from animals sacrificed two to three days after the final immunization. Antibody-producing cells include spleen cells, lymph node cells, and peripheral blood cells. Spleen cells are generally used. Specifically, tissues such as spleens or lymph nodes are excised or collected from the various animals described above. Then, the tissues are crushed and the resulting material is suspended in a medium or buffer, such as PBS, DMEM, or RPMI1640, followed by filtration with a stainless mesh or the like. This is then centrifuged to obtain antibody-producing cells of interest.

The above-described myeloma cells and antibody-producing cells are then fused. Cell fusion is achieved by contacting the myeloma cells with the antibody-producing cells at a ratio of 1:1 to 1:20 in a medium for animal cell culture, such as MEM, DMEM, and RPMI-1640, at 30 to 37° C. for one to 15 minutes in the presence of a fusion-promoting agent. To promote cell fusion, the antibody-producing cells and the myeloma cells may be fused using a commercially available cell-fusion device, using a fusion-promoting agent, such as polyethylene glycol (mean molecular weight 1,000 to 6,000 (Da)) or polyvinyl alcohol, or a virus for fusion, such as Sendai virus.

Hybridomas of interest are selected from the cells after cell fusion. The selection methods include methods using selective propagation of cells in a selective medium. Specifically, a cell suspension is diluted with an appropriate medium, and then the cells are plated on to microtiter plates. An aliquot of selection medium (for example, HAT medium) is added to each well, and then the cells are cultured while the selection medium is appropriately exchanged. The cells grown as a result can be saved as hybridomas.

In another embodiment, antibodies or antibody fragments can be isolated from an antibody phage library, produced by using the technique reported by McCafferty et al. (Nature 348:552-554 (1990)). Clackson et al. (Nature 352:624-628 (1991)) and Marks et al . (J. Mol. Biol. 222:581-597 (1991)) reported on the respective isolation of mouse and human antibodies from phage libraries. There are also reports that describe the production of high affinity (nM range) human antibodies based on chain shuffling (Marks et al., Bio/Technology 10:779-783 (1992)), and combinatorial infection and in vivo recombination, which are methods for constructing large-scale phage libraries (Waterhouse et al., Nucleic Acids Res. 21:2265-2266 (1993)). These technologies can also be used to isolate monoclonal antibodies, instead of using conventional hybridoma technology for monoclonal antibody production.

The non-neutralizing anti-aPC antibodies of the present invention can be selected, for example, by the screening method described below:

1st Screening

To select antibodies which bind to aPC, each antibody is assessed for its binding specificity using a known technique, such as EIA (enzyme immunoassay), RIA (radioimmunoassay), ELISA (enzyme-linked immunosorbent assay), HTRF (homogenous time-resolved fluorescence), or fluorescence immunoassay (Antibodies A Laboratory Manual. Ed Harlow, David Lane, Cold Spring Harbor Laboratory, 1988).

2nd Screening

APTT (activated partial thromboplastin time) is determined using human blood plasma, to select antibodies which potentiate the anticoagulant activity of aPC. Alternatively, aPC inactivation is assessed by combining aPC with AAT or PCI, to select antibodies which inhibit aPC inactivation by AAT and/or PCI. For example, when the assay comprises the use of antibodies prepared from antibody-producing cells (for example, hybridomas), the antibody-producing cells which produce antibodies comprising the activity of interest are identified and cloned by the limiting dilution method. The clones are grown using standard methods (Goding, Monoclonal Antibodies: Principals an Practice, pp. 59-103, Academic Press, 1986). The cells may be cultured in a medium, for example, D-MEM or RPIM-1640 medium. Such antibody-producing cells can be cloned by repeating the screening, which comprises selecting cells (for example, hybridomas) that produce antibodies which more strongly suppress aPC inactivation.

The antibodies of the present invention are antibodies that suppress aPC inactivation caused by blood or an aPC inhibitor. The level of suppression is defined as the inactivation suppression rate (%). The level is expressed as a relative value, taking the activity of aPC inactivated by blood or an aPC inhibitor as 0%, and that of aPC without inactivation as 100%.

The inactivation suppression rate may be determined under optimal conditions by appropriately changing the antibody concentration. Specifically, the rate can be determined as follows: 10 μL of 10 μg/mL aPC (for example, SIGMA, P-2200) solution is combined with 40 μL of an antibody solution (e.g., a hybridoma culture supernatant, yielded during hybridoma screening) or a control solution without antibody (e.g., culture supernatant of myeloma cells, or HAT medium). The resulting mixture is incubated at room temperature for a certain period of time (for example, for 60 minutes). 50 μL of blood plasma (e.g., standard human plasma) is added to the mixture and also incubated at room temperature for a certain period of time (for example, for 60 minutes). 50 μL of APTT reagent (e.g., DADE BEHRING, GAA-200A) is added to the mixture. The blood coagulation time for an aPC sample incubated without blood plasma is determined by adding aPC to blood plasma immediately prior to the addition of APTT reagent. For example, 50 μL of 20 mmol/L $CaCl_2$ (e.g., DADE BEHRING, GMZ-310) is added to the solution after incubation at 37° C. for three minutes, and the time required for coagulation is then determined. Blood coagulation time can be determined using an automatic analyzer for blood coagulation (e.g., Amelung, KC-10A), or such.

Coagulation time (a) is taken as 100% when aPC incubated without blood plasma is added, and coagulation time (b) is taken as 0% when aPC incubated with blood plasma is added after incubation with a control solution without antibody (e.g., the supernatant of myeloma cell culture described above). Based on the coagulation time (c), when aPC incubated with blood plasma is added after incubation with an antibody solution, such as a hybridoma culture supernatant, the antibody solution, such as the hybridoma culture supernatant, is assessed for its activity to extend coagulation time: (inactivation suppression rate (%)={(c−b)/(a−b)}×100) . As this value increases, the activity of suppressing aPC inactivation is judged to be higher. Likewise, when aPC activity is assessed using a substrate compound, such as S-2366, the inactivation suppression rate (%) can be determined by assessing aPC activity in comparison with the activity of aPC inactivated by blood plasma but incubated without antibody, and the activity of aPC incubated without blood plasma. The inactivation suppression rate (%) for an antibody of the present invention is preferably ten or higher, more preferably 15 or higher, more preferably 18 or higher, more preferably 20 or higher, more preferably 25 or higher, more preferably 30 or higher, more preferably 35 or higher, more preferably 40 or higher, more preferably 45 or higher, and more preferably 50 or higher.

In addition, an antibody of the present invention preferably comprises the activity of inhibiting aPC inactivation by an aPC inhibitor, such as PCI or AAT. This activity can be determined by chromogenic assay using a low-molecular-weight substrate. For example, 40 µL of a solution of a purified antibody and 10 µL of 10 µg/mL aPC solution are combined and incubated at room temperature for 60 minutes. 50 µL of the mixture containing aPC and the antibody is added to a buffer (final concentrations: 70 mmol/L Tris (pH 8.0), 125mmol/L NaCl, 10 mmol/L $CaCl_2$, and0.1% BSA) comprising 10 U heparin, and the total volume is adjusted to 180 µL. 20 µL of 100 µg/mL recombinant PCI (with Flag tag) is added to the mixture, and the resulting mixed solution is incubated at 37° C. for 30 minutes. 50 µL of the low-molecular-weight substrate S-2366 (2 mmol/L) is added to the mixture. The absorbance (at 405 nm) of the resulting mixture is determined after 60 minutes.

As PCI is added, absorbance is decreased compared to that of aPC in the absence of PCI. The relative activity of the antibody is determined based on the mean absorbance, taking aPC activity in the presence of PCI as 0%, and aPC activity in the absence of PCI as 100%. For an antibody of the present invention, the relative value is preferably one or higher, more preferably two or higher, more preferably three or higher, more preferably five or higher, more preferably seven or higher, more preferably ten or higher, and more preferably twelve or higher.

An antibody of the present invention may be an antibody, for example, comprising anticoagulant activity assessed by the APTT assay using blood plasma described above, or the activity of inhibiting aPC inactivation by PCI described above. More preferably, an antibody of the present invention comprises both activities. Specifically, a preferred antibody of the present invention is an antibody which suppresses aPC inactivation by blood and by an aPC inhibitor.

An antibody of the present invention may be an antibody, for example, which binds to an aPC site with which a physiological aPC inhibitor interacts. Such amino acids of aPC have been identified, and include, for example, E215, S216, and S336 (Shen, L., Biochemistry 39:2853-2860 (2000)). An antibody of the present invention may be an antibody which binds to any of these amino acids in aPC, or near to these amino acids (e.g., within a range of ten amino acids). Such an antibody can be prepared by synthesizing an oligopeptide that comprises a target portion of aPC, and immunizing animals with the peptide as an antigen. Known active sites of aPC are H211, D257, and S360 (Foster, D. C., Proc. Natl. Acad. Sci. USA 82:4673-4677 (1985)). Antibodies which bind to any of the regions comprising these amino acids are unfavorable, since such antibodies may inhibit the activity of aPC.

Methods for preparing monoclonal antibodies from the obtained hybridomas include standard cell culture methods and methods comprising ascites production. In cell culture methods, hybridomas are cultured for two to 14 days under standard culture conditions (for example, at 37° C. at 5% $CO_2$ atmosphere), in a culture medium for animal cells, such as RPMI-1640 or MEM containing 10 to 20% fetal calf serum, or serum-free medium, and antibodies are then prepared from the culture supernatant. In the method comprising ascites production, hybridomas are administered to the peritoneal cavities of mammalian individuals of the same species as that from which the myeloma cells are derived, and the hybridomas proliferate in to large quantities. Ascites or serum is then collected after one to four weeks. To enhance ascites production, for example, pristane (2,6,10,14-tetramethylpentadecane) may be pre-administered to the peritoneal cavity.

Antibodies to be used in the present invention can be purified by a method appropriately selected from known methods, such as the protein A-Sepharose method, hydroxyapatite chromatography, salting-out method with sulfate, ion exchange chromatography, and affinity chromatography, or by the combined use of the same.

The present invention may use recombinant antibodies, produced by gene engineering. The genes encoding the antibodies obtained by a method described above are isolated from the hybridomas. The genes are inserted into an appropriate vector, and then introduced into a host (see, e.g., Carl, A. K. Borrebaeck, James, W. Larrick, Therapeutic Monoclonal Antibodies, Published in the United Kingdom by Macmillan Publishers Ltd, 1990). The present invention provides the nucleic acids encoding the antibodies of the present invention, and vectors comprising these nucleic acids. Specifically, using a reverse transcriptase, cDNAs encoding the variable regions (V regions) of the antibodies are synthesized from the mRNAs of hybridomas. After obtaining the DNAs encoding the variable regions of antibodies of interest, they are ligated with DNAs encoding desired constant regions (C regions) of the antibodies, and the resulting DNA constructs are inserted into expression vectors. Alternatively, the DNAs encoding the variable regions of the antibodies may be inserted into expression vectors comprising the DNAs of the antibody C regions. These are inserted into expression vectors so that the genes are expressed under the regulation of an expression regulatory region, for example, an enhancer and promoter. Then, host cells are transformed with the expression vectors to express the antibodies. The present invention provides cells expressing antibodies of the present invention. The cells expressing antibodies of the present invention include cells and hybridomas transformed with a gene of such an antibody.

A particularly preferred antibody of the present invention binds to an epitope that overlaps with (or is identical to) any of the monoclonal antibodies isolated in the Examples (Table 1). In the present invention, such an antibody is referred to as an "antibody that binds to a substantially identical site". For example, an antibody which binds to a site substantially identical to a site in aPC to which a monoclonal antibody described in the Examples binds, can be obtained by analyzing epitopes of the above-described monoclonal antibody using a known method of epitope mapping using partial aPC peptides or the like, and then preparing antibodies that bind to a peptide comprising the identified epitope, which is used as an antigen. Such an antibody is expected to comprise a suppressing activity similar to that of the antibodies isolated as preventing the decrease of aPC activity in the Examples. Competitive assays, for example, can be used to determine whether or not two antibodies bind to a substantially identical site on an antigen protein. Specifically, when the binding of the first anti-aPC antibody with aPC is competitively inhibited by the second anti-aPC antibody, the first antibody and the second antibody can be judged to bind to a substantially identical site in the antigen. Thus, the present invention includes antibodies which bind to a site substantially identical to a site in aPC to which an antibody isolated in the Examples binds, and which comprise the activity of inhibiting aPC inactivation by blood and/or by an aPC inhibitor.

The antibodies of the present invention also include antibodies which comprise the complementarity-determining regions (CDRs) of any of the monoclonal antibodies isolated in the Examples (Table 1), or complementarity-determining regions functionally equivalent thereto. The term "functionally equivalent" refers to comprising amino acid sequences similar to the amino acid sequences of CDRs of any of the monoclonal antibodies isolated in the Examples, and comprising the activity of inhibiting aPC inactivation by blood and/or by an aPC inhibitor. The term "CDR" refers to a region in an antibody variable region (also called "V region"), and determines the specificity of antigen binding. The H chain and L chain each have three CDRs, designated from the N terminus as CDR1, CDR2, and CDR3. There are four regions flanking these CDRs: these regions are referred to as "framework", and their amino acid sequences are highly conserved. The CDRs can be transplanted into other antibodies, and thus a recombinant antibody can be prepared by combining CDRs with the framework of a desired antibody. One or more amino acids of a CDR can be modified without losing the ability to bind to its antigen. For example, one or more amino acids in a CDR can be substituted, deleted, and/or added.

An amino acid residue is preferably mutated into one that allows the properties of the amino acid side-chain to be conserved. Examples of the properties of amino acid side chains comprise: hydrophobic amino acids (A, I, L, M, F, P, W, Y, V), hydrophilic amino acids (R, D, N, C, E, Q, G, H, K, S, T), and amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chains (R, K, H); and aromatic-containing side-chains (H, F, Y, W). (The letters within parenthesis indicate the one-letter amino acid codes.) Amino acid substitutions within each group are called conservative substitutions. It is well known that a polypeptide comprising a modified amino acid sequence in which one or more amino acid residues is deleted, added, and/or substituted can retain the original biological activity (Mark D. F. et al., Proc. Natl. Acad. Sci. U.S.A. 81:5662-5666 (1984); Zoller M. J. and Smith M., Nucleic Acids Res. 10: 6487-6500 (1982); Wang A. et al., Science 224: 1431-1433; Dalbadie-McFarland G. et al., Proc. Natl. Acad. Sci. U.S.A. 79: 6409-6413 (1982)). The number of mutated amino acids is not limited, but in general, the number falls within 40% of amino acids of each CDR, and preferably within 35%, and still more preferably within 30% (e.g., within 25%). The identity of amino acid sequences can be determined as described herein.

The antibodies of the present invention include antibodies which comprise CDRs functionally equivalent to the CDRs of #79, #123, #281, or #285, described in the Examples. Such antibodies include, for example, antibodies which comprise three CDRs comprising the amino acid sequences, DSYMN (SEQ ID NO: 9), EVYPETGNSYYNEKFKG (SEQ ID NO: 10), and GGTGFDY (SEQ ID NO: 11), or CDRs functionally equivalent to these CDRs. The amino acid sequences shown above correspond to CDR1, CDR2, and CDR3 of the antibody H chain, respectively. An antibody of the present invention can be prepared by substituting these CDRs for the corresponding CDR1, CDR2, and CDR3 between the framework of a desired heavy chain variable region. Each of the amino acids in the above-described CDRs may be appropriately changed by amino acid substitution or such. For example, the antibodies of the present invention include antibodies comprising each of the CDRs whose amino acids have been conservatively substituted. Such antibodies are expected to have an activity equivalent to that of clone #79.

In an above-described antibody comprising heavy chain CDRs, the CDRs can be combined with appropriate variable regions of an antibody L chain. L chain CDRs preferably combined with heavy chain CDRs are, for example, CDRs comprising the amino acid sequences of TASSSVSSSYLH (SEQ ID NO: 21), STSNLASGAPT (SEQ ID NO: 22), and YHRSPFT (SEQ ID NO: 23), or CDRs functionally equivalent to these CDRs. The respective amino acid sequences correspond to CDR1, CDR2, and CDR3 of an antibody L chain. Alternatively, these L chain CDRs may be used independently of the heavy chains described above. The CDRs are substituted for the corresponding CDR1, CDR2, and CDR3, between the framework of a desired L chain variable region. The respective amino acids of the CDRs described above may be changed by an appropriate procedure, such as substitution. For example, the antibodies of the present invention include antibodies which comprise each of the CDRs whose amino acids have been conservatively substituted.

Specifically, the antibodies of the present invention include antibodies which comprise the activity of inhibiting aPC inactivation by blood and/or by an aPC inhibitor, with heavy chains comprising:

(a) CDRs comprising the amino acid sequences of SEQ ID NOs: 9, 10, and 11;
(b) CDRs comprising amino acid sequences in which arbitrary amino acid(s) have been substituted conservatively in SEQ ID NOs: 9, 10, and 11;
(c) CDRs comprising the amino acid sequences in which two or fewer amino acids of SEQ ID NO: 9, eight or fewer amino acids of SEQ ID NO: 10, and three or fewer amino acids of SEQ ID NO: 11 have been substituted, deleted, and/or added; or
(d) CDRs comprising amino acid sequences which are 70% or more identical to the amino acid sequences of SEQ ID NOs: 9, 10, and 11.

Herein, the number of amino acids modified in (c) is preferably one in SEQ ID NO: 9. In SEQ ID NO: 10, the number is preferably seven or less, more preferably six or less, more preferably five or less, more preferably four or less, more preferably three or less, and more preferably two or one. In SEQ ID NO: 11, the number is preferably two or one, and more preferably one. The identity in (d) is preferably 75% or higher, more preferably 80% or higher, more preferably 90% or higher, and still more preferably 95% or higher.

Further, the antibodies of the present invention include antibodies which comprise the activity of inhibiting aPC inactivation by blood and/or an aPC inhibitor, with L chains comprising:

(a) CDRs comprising the amino acid sequences of SEQ ID NOs: 21, 22, and 23;
(b) CDRs comprising amino acid sequences in which arbitrary amino acid(s) have been conservatively substituted in SEQ ID NOs: 21, 22, and 23;
(c) CDRs comprising amino acid sequences in which five or fewer amino acids of SEQ ID NO: 21, five or fewer amino acids of SEQ ID NO: 22, and three or fewer amino acids of SEQ ID NO: 23 have been substituted, deleted, and/or added; or
(d) CDRs comprising amino acid sequences which are 70% or more identical to the amino acid sequences of SEQ ID NOs: 21, 22, and 23, wherein, the number of amino acids modified in (c) is preferably four or less, more preferably three or less, more preferably two or less, and more preferably one in SEQ ID NO: 21. In SEQ ID NO: 22, the number is more preferably four or less, more preferably three or less, more preferably two or less, and more preferably one. In SEQ ID NO: 23, the number is preferably two or less, and more preferably one. Identity in (d) is preferably 75% or higher, more preferably 80% or higher, more preferably 90% or higher, and still more preferably 95% or higher. Antibodies comprising the CDRs of both heavy and light chains are particularly preferable as the antibodies of the present invention.

The antibodies of the present invention also include antibodies with CDRs comprising the amino acid sequences of (S/R)SWMN (SEQ ID NO: 31), RIYPGDGD(T/S)(N/I)YN-GKF(R/K)G (SEQ ID NO: 32), and WG(I/S) (T/S) (T/G) (A/S) (A/S)WFAY (SEQ IDNO: 33), or CDRs functionally equivalent thereto. As described above, the amino acid sequences respectively correspond to CDR1, CDR2, and CDR3 of an antibody H chain. More specific examples of preferred amino acid sequences of such antibody heavy chain CDRs include SSWMN (SEQ ID NO: 12) and RSWMN (SEQ ID NO: 18) for CDR1, RIYPGDGDTNYNGKFRG (SEQ ID NO: 13) and RIYPGDGDSIYNGKFKG (SEQ ID NO: 19) for CDR2, and WGITTAAWFAY (SEQ ID NO: 14) and WGSSGSSWFAY (SEQ IDNO: 20) for CDR3. Specifically, CDR1, CDR2, and CDR3 of the heavy chain of the monoclonal antibody #123 or #285 can be used in combination. Such an antibody is expected to comprise an activity equivalent to that of #123 or #285. In such cases, as the L chain CDRs, it is preferable to use combinations of, for example, those comprising the amino acid sequences of RTS-ENIYSYLA (SEQ ID NO: 24), NAKTLAEGVPS (SEQ ID NO: 25), and YYG (T/S) P (P/Y) T (SEQ ID NO: 34), or CDRs functionally equivalent thereto. These respective amino acid sequences correspond to CDR1, CDR2, and CDR3 of an antibody L chain. Alternatively, these L chain CDRs maybe used independently of the heavy chains described above. More specific examples of preferred amino acid sequences of L chain CDR3 to be used include YYGT-PPT (SEQ ID NO: 26) and YYGSPYT (SEQ ID NO: 30), but are not limited thereto.

Specifically, the antibodies of the present invention include antibodies which comprise the activity of inhibiting aPC inactivation by blood and/or by an aPC inhibitor, and which have heavy chains comprising:

(a) CDRs comprising the amino acid sequences of SEQ ID NOs: 31, 32, and 33;

(b) CDRs comprising amino acid sequences in which arbitrary amino acid(s) have been conservatively substituted in SEQ ID NOs: 31, 32, and 33;

(c) CDRs comprising amino acid sequences in which two or fewer amino acids of SEQ ID NO: 31, eight or fewer amino acids of SEQ ID NO: 32, and five or fewer amino acids of SEQ ID NO: 33 have been substituted, deleted, and/or added; or (d) CDRs comprising amino acid sequences which are 70% or more identical to the amino acid sequences of SEQ ID NOs: 31, 32, and 33, wherein the number of amino acids modified in (c) is preferably one in SEQ ID NO: 31. In SEQ ID NO: 32, the number is preferably seven or less, more preferably six or less, more preferably five or less, more preferably four or less, more preferably three or less, and more preferably two or one. In SEQ ID NO: 33, the number is preferably four or less, more preferably three or less, more preferably two or less, and more preferably one. Identity in (d) is preferably 75% or higher, more preferably 80% or higher, more preferably 90% or higher, and still more preferably 95% or higher.

Further, the antibodies of the present invention include antibodies which comprise the activity of inhibiting aPC inactivation by blood and/or by an aPC inhibitor, and which have L chains comprising:

(a) CDRs comprising the amino acid sequences of SEQ ID NOs: 24, 25, and 34;

(b) CDRs comprising amino acid sequences in which arbitrary amino acid(s) have been conservatively substituted in SEQ ID NOs: 24, 25, and 34;

(c) CDRs comprising the amino acid sequences in which five or fewer amino acids of SEQ ID NO: 24, five or fewer amino acids of SEQ ID NO: 25, and four or fewer amino acids of SEQ ID NO: 34 have been substituted, deleted, and/or added; or (d) CDRs comprising amino acid sequences which are 70% or more identical to the amino acid sequences of SEQ ID NOs: 24, 25, and 34, where in (c) the number of amino acids modified is preferably four or less, more preferably three or less, more preferably two or less, and more preferably one in SEQ ID NO: 24. In SEQ ID NO: 25, the number is preferably four or less, more preferably three or less, more preferably two or less, and more preferably one. In SEQ ID NO: 34, the number is preferably three or less, more preferably two or less, and more preferably one. The identity in (d) is preferably 75% or higher, more preferably 80% or higher, more preferably 90% or higher, and still more preferably 95% or higher. Antibodies comprising the CDRs of both heavy and light chains are particularly preferable as the antibodies of the present invention.

The antibodies of the present invention also include antibodies which have CDRs comprising the amino acid sequences of DYSLH (SEQ ID NO: 15), WINTETGEPTY-ADDLKG (SEQ ID NO: 16), and GITLDY (SEQ ID NO: 17), or CDRs functionally equivalent thereto. As described above, the amino acid sequences correspond to CDR1, CDR2, and CDR3 of an antibody H chain, respectively. Such an antibody is expected to comprise an activity equivalent to that of #281. In this case, as the L chain CDRs, it is preferable to use combinations of, for example, those CDRs comprising the amino acid sequences of KSSQSLLSSSNQKNFLA (SEQ ID NO: 27), SWASTRHSGVPD (SEQ ID NO: 28), and YYRYPLT (SEQ ID NO: 29), or CDRs functionally equivalent thereto. The amino acid sequences correspond to CDR1, CDR2, and CDR3 of an antibody L chain, respectively.

Specifically, the antibodies of the present invention include antibodies which comprise the activity of inhibiting aPC inactivation by blood and/or by an aPC inhibitor, and which have heavy chains comprising:

(a) CDRs comprising the amino acid sequences of SEQ ID NOs: 15, 16, and 17;

(b) CDRs comprising amino acid sequences in which arbitrary amino acid(s) have been conservatively substituted in SEQ ID NOs: 15, 16, and 17;

(c) CDRs comprising amino acid sequences in which two or fewer amino acids of SEQ ID NO: 15, eight or fewer amino acids of SEQ ID NO: 16, and five or fewer amino acids of SEQ ID NO: 17 have been substituted, deleted, and/or added; or (d) CDRs comprising amino acid sequences which are 70% or more identical to the amino acid sequences of SEQ ID NOs: 15, 16, and 17.

In (c), the number of amino acids modified is preferably one in SEQ ID NO: 15. In SEQ ID NO: 16, the number is preferably seven or less, more preferably six or less, more preferably five or less, more preferably four or less, and more preferably three or less. In SEQ ID NO: 17, the number is preferably four or less, more preferably three or less, more preferably two or less, and more preferably one. Identity in (d) is preferably 75% or higher, more preferably 80% or higher, more preferably 90% or higher, and still more preferably 95% or higher.

Further, the antibodies of the present invention include antibodies which comprise the activity of inhibiting aPC inactivation by blood and/or by an aPC inhibitor, and which have L chains comprising:
(a) CDRs comprising the amino acid sequences of SEQ ID NOs: 27, 28, and 29;
(b) CDRs comprising amino acid sequences in which arbitrary amino acid(s) have been conservatively substituted in SEQ ID NOs: 27, 28, and 29;
(c) CDRs comprising amino acid sequences in which eight or fewer amino acids of SEQ ID NO: 27, five or fewer amino acids of SEQ ID NO: 28 and three or fewer amino acids of SEQ ID NO: 29 have been substituted, deleted, and/or added; or
(d) CDRs comprising amino acid sequences which are 70% or more identical to the amino acid sequences of SEQ ID NOs: 27, 28, and 29.

In (c), the number of amino acids modified is preferably seven or less, more preferably six or less, more preferably five or less, more preferably four or less, more preferably three or less, more preferably two or less, and more preferably one in SEQ ID NO: 27. In SEQ IDNO: 28, the number is preferably four or less, more preferably three or less, more preferably two or less, and more preferably one. In SEQ ID NO: 29, the number is preferably two or less, and more preferably one. Identity in (d) is preferably 75% or higher, more preferably 80% or higher, more preferably 90% or higher, and still more preferably 95% or higher. Antibodies comprising the CDRs of both heavy and light chains are particularly preferable as the antibodies of the present invention.

The antibodies of the present invention include an antibody which has an antibody H chain variable region comprising the amino acid sequence of SEQ ID NO: 1, 2, 3, or 4, or a variable region functionally equivalent thereto. In this case, it is preferable to use combinations of L chains, for example, which have a variable region comprising the amino acid sequence of SEQ ID NO: 5, 6, 7, or 8, or variable regions functionally equivalent thereto. Specifically, the antibodies of the present invention include antibodies which comprise the activity of inhibiting aPC inactivation by blood and/or by an aPC inhibitor, with heavy chains comprising:
(a) a variable region comprising an amino acid sequence of SEQ ID NO: 1, 2, 3, or 4;
(b) a variable region comprising an amino acid sequence in which an arbitrary amino acid(s) has been conservatively substituted in SEQ ID NO: 1, 2, 3, or 4;
(c) a variable region comprising an amino acid sequence in which one or more amino acids have been substituted, deleted, and/or added in SEQ ID NO: 1, 2, 3, or 4; or
(d) a variable region comprising an amino acid sequence which is 70% or more identical to an amino acid sequence of SEQ ID NO: 1, 2, 3, or 4.

In (c), the number of amino acids modified is preferably 30 or less, more preferably 25 or less, more preferably 20 or less, more preferably 15 or less, more preferably 10 or less, and more preferably 5 or less. Identity in (d) is preferably 75% or higher, more preferably 80% or higher, more preferably 90% or higher, and still more preferably 95% or higher.

Further, the antibodies of the present invention include antibodies which comprise the activity of inhibiting aPC inactivation by blood and/or by an aPC inhibitor, with L chains comprising:
(a) a variable region comprising an amino acid sequence of SEQ ID NO: 5, 6, 7, or 8;
(b) a variable region comprising an amino acid sequence in which an arbitrary amino acid(s) has been conservatively substituted in SEQ ID NO: 5, 6, 7, or 8;
(c) a variable region comprising an amino acid sequence in which one or more amino acids have been substituted, deleted, and/or added in SEQ ID NO: 5, 6, 7, or 8; or
(d) a variable region comprising an amino acid sequence which is 70% or more identical to an amino acid sequence of SEQ ID NO: 5, 6, 7, or 8.

In (c), the number of amino acids modified is preferably 30 or less, more preferably 25 or less, more preferably 20 or less, more preferably 15 or less, more preferably 10 or less, and more preferably 5 or less. Identity in (d) is preferably 75% or higher, more preferably 80% or higher, more preferably 90% or higher, and still more preferably 95% or higher. An antibody comprising both an H chain variable region and an L chain variable region, described above, is particularly preferable as an antibody of the present invention.

The amino acid sequences can be modified, for example, by synthesizing multiple oligonucleotides encoding the amino acid sequence of a modified variable region, and preparing nucleic acids encoding the variable region by PCR using the oligonucleotides. Antibodies which comprise desired CDRs can be prepared by inserting the nucleic acid into an appropriate expression vector and expressing it. For example, the oligonucleotides are synthesized using mixed nucleotides to prepare a DNA library that encodes a variety of antibodies comprising CDRs with various amino acids introduced at certain positions. An antibody of the present invention can be isolated by selecting from the library a clone encoding an antibody which binds to aPC and inhibits the suppression of its activity. The present invention relates to the nucleic acids encoding the antibodies of the present invention, vectors comprising these nucleic acids, and host cells comprising the nucleic acids or the vectors. The nucleic acids may be DNAs or RNAs. The vectors include known vectors, such as plasmids, phages, and viral vectors. The host cells include bacteria, yeasts, insects, plant cells, and mammalian cells.

In the present invention, recombinant antibodies artificially modified to reduce heterologous antigenicity against humans can be used. Examples include chimeric antibodies and humanized antibodies. These modified antibodies can be produced using known methods. A chimeric antibody includes an antibody comprising variable and constant regions of species that are different to each other, for example, an antibody comprising the antibody heavy chain and light chain variable regions of a nonhuman mammal such as a mouse, and the antibody heavy chain and light chain constant regions of a human. Such an antibody can be obtained by (1) ligating a DNA encoding a variable region of a mouse antibody to a DNA encoding a constant region of a human antibody; (2) incorporating this into an expression vector; and (3) introducing the vector into a host for production of the antibody.

A humanized antibody, which is also called a reshaped human antibody, is obtained by substituting an H or L chain complementarity determining region (CDR) of an antibody of a nonhuman mammal such as a mouse, with the CDR of a human antibody. Conventional genetic recombination techniques for the preparation of such antibodies are known (see, for example, Jones et al., Nature 321: 522-525 (1986); Reichmann et al., Nature 332: 323-329 (1988); Presta Curr. Op. Struct. Biol. 2: 593-596 (1992)). Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by (1) ligating the resulting DNA to a DNA that encodes a human antibody constant region; (2)

incorporating this into an expression vector; and (3) transfecting the vector into a host to produce the antibody (see, European Patent Application No. EP 239,400, and International Patent Application No. WO 96/02576). Human antibody FRs that are ligated via the CDR are selected where the CDR forms a favorable antigen-binding site. The humanized antibody may comprise additional amino acid residue(s) that are not included in the CDRs introduced into the recipient antibody, nor in the framework sequences. Such amino acid residues are usually introduced to more accurately optimize the antibody's ability to recognize and bind to an antigen. For example, as necessary, amino acids in the framework region of an antibody variable region may be substituted such that the CDR of a reshaped human antibody forms an appropriate antigen-binding site (Sato, K. et al., Cancer Res. (1993) 53, 851-856).

Methods for obtaining human antibodies are also known. For example, desired human antibodies with antigen-binding activity can be obtained by (1) sensitizing human lymphocytes with antigens of interest or cells expressing antigens of interest in vitro; and (2) fusing the sensitized lymphocytes with human myeloma cells such as U266 (see Examined Published Japanese Patent Application No. (JP-B) Hei 1-59878). Alternatively, the desired human antibody can also be obtained by using an antigen to immunize a transgenic (Tg) animal that comprises a partial or entire repertoire of human antibody genes (see Nature Genetics 7:13-21 (1994); Nature Genetics 15:146-156 (1997); Nature 368:856-859 (1994); International Patent Application WO 93/12227, WO 92/03918, WO 94/02602, WO 94/25585, WO 96/34096, and WO 96/33735). Specifically, such Tg animals are created as follows: a nonhuman mammal in which the loci of heavy and light chains of an endogenous immunoglobulin have been disrupted, and instead, the loci of heavy and light chains of a human immunoglobulin have been introduced via Yeast artificial chromosome (YAC) vectors and the like, is obtained by creating knockout animals or Tg animals, or mating such animals. The immunoglobulin heavy chain loci can be functionally inactivated, for example, by introducing a defect at a certain site in a J region or C region (e.g., Cμ region). The immunoglobulin light chains (e.g., κ chain) can be functionally inactivated, for example, by introducing a defect at a certain site in a J region or C region, or a region comprising the J and C regions.

Such a humanized antibody can also be obtained from culture supernatant, by using genetic engineering technology to transform eukaryotic cells with cDNAs that encode each of the heavy and light chains of the antibody, or preferably vectors comprising these cDNAs, and then culturing the transformed cells that produce the recombinant human monoclonal antibody. The hosts are, for example, desired eukaryotic cells, preferably mammalian cells, such as CHO cells, lymphocytes, and myelomas.

Furthermore, techniques to obtain human antibodies by panning with a human antibody library are known. For example, the variable region of a human antibody is expressed as a single chain antibody (scFv) on the surface of a phage, using phage display method, and phages that bind to the antigen can be selected. By analyzing the genes of selected phages, the DNA sequences encoding the variable regions of human antibodies that bind to the antigen can be determined. If the DNA sequences of scFvs that bind to the antigen are identified, appropriate expression vectors comprising these sequences can be constructed, and then introduced into appropriate hosts and expressed to obtain human antibodies. Such methods are already well known (see WO 92/01047, WO 92/20791, WO 93/06213, WO 93/11236, WO 93/19172, WO 95/01438, and WO 95/15388).

When the antibody genes have been isolated and introduced into an appropriate host, hosts and expression vectors can be used in appropriate combination to produce the antibodies. As eukaryotic host cells, animal cells, plant cells, and fungal cells may be used. The animal cells include: (1) mammalian cells such as CHO, COS, myeloma, baby hamster kidney (BHK), HeLa, and Vero cells; (2) amphibian cells such as Xenopus oocytes; or (3) insect cells such as sf9, sf21, and Tn5, or silkworms. Known plant cells include cells derived from the *Nicotiana* genus such as *Nicotiana tabacum*, which can be callus cultured. Known fungal cells include yeasts such as the *Saccharomyces* genus, for example *Saccharomyces cerevisiae*, and filamentous fungi such as the *Aspergillus* genus, for example *Aspergillus niger*. Prokaryotic cells can also be used in production systems that utilize bacterial cells. Known bacterial cells include *E. coli* and *Bacillus subtilis*. The antibodies can be obtained by transferring the antibody genes of interest into these cells using transformation, and then culturing the transformed cells in vitro.

The isotypes of the antibodies of the present invention are not limited. The isotypes include, for example, IgG (IgG1, IgG2, IgG3, and IgG4), IgM, IgA (IgA1 and IgA2), IgD, and IgE, but IgG and IgM are preferable. The antibodies of the present invention may also be antibody fragments comprising a portion responsible for antigen binding, or a modified fragment thereof. The term "antibody fragment" refers to a portion of a full-length antibody, and generally to a fragment comprising an antigen-binding domain or a variable region. Such antibody fragments include, for example, Fab, $F(ab')_2$, Fv, single-chain Fv (scFv) which comprises a heavy chain Fv and a light chain Fv coupled together with an appropriate linker, diabody (diabodies), linear antibodies, and multispecific antibodies prepared from antibody fragments. Previously, antibody fragments were produced by digesting natural antibodies with a protease; currently, methods for expressing them as recombinant antibodies using genetic engineering techniques are also known (see Morimoto et al., Journal of Biochemical and Biophysical Methods 24:107-117 (1992); Brennan et al., Science 229:81 (1985); Co, M. S. et al., J. Immunol., 1994, 152, 2968-2976; Better, M. & Horwitz, A. H., Methods in Enzymology, 1989, 178, 476-496, Academic Press, Inc.; Plueckthun, A. & Skerra, A., Methods in Enzymology, 1989, 178, 476-496, Academic Press, Inc.; Lamoyi, E., Methods in Enzymology, 1989, 121, 663-669; Bird, R. E. et al., TIBTECH, 1991, 9, 132-137).

An "Fv" fragment is the smallest antibody fragment, and contains a complete antigen recognition site and a binding site. This region is a dimer ($V_H$-$V_L$ dimer) wherein the variable regions of each of the heavy chain and light chain are strongly connected by a noncovalent bond. The three CDRs of each of the variable regions interact with each other to form an antigen-binding site on the surface of the $V_H$-$V_L$ dimer. In other words, a total of six CDRs from the heavy and light chains function together as an antibody's antigen-binding site. However, a variable region (or a half Fv, which contains only three antigen-specific CDRS) alone is also known to be able to recognize and bind to an antigen, although its affinity is lower than the affinity of the entire binding site. Thus, a preferred antibody fragment of the present invention is an Fv fragment, but is not limited thereto. Such an antibody fragment may be a polypeptide which comprises an antibody fragment of heavy or light chain CDRs which are conserved, and which can recognize and bind its antigen.

A Fab fragment (also referred to as F(ab)) also contains a light chain constant region and heavy chain constant region (CH1). For example, papain digestion of an antibody produces the two kinds of fragments: an antigen-binding fragment, called a Fab fragment, containing the variable regions of a heavy chain and light chain, which serve as a single antigen-binding domain; and the remaining portion, which is called an "Fc" because it is readily crystallized. A Fab' fragment is different from a Fab fragment in that a Fab' fragment also has several residues derived from the carboxyl terminus of a heavy chain CH1 region, which contains one or more cysteine residues from the hinge region of an antibody. A Fab' fragment is, however, structurally equivalent to Fab in that both are antigen-binding fragments which comprise the variable regions of a heavy chain and light chain, which serve as a single antigen-binding domain. Herein, an antigen-binding fragment comprising the variable regions of a heavy chain and light chain which serve as a single antigen-binding domain, and which is equivalent to that obtained by papain digestion, is referred to as a "Fab-like antibody", even when it is not identical to an antibody fragment produced by protease digestion. Fab'-SH is Fab' with one or more cysteine residues having free thiol groups in its constant region. A F(ab') fragment is produced by cleaving the disulfide bond between the cysteine residues in the hinge region of $F(ab')_2$. Other chemically crosslinked antibody fragments are also known to those skilled in the art. Pepsin digestion of an antibody yields two fragments; one is a $F(ab')_2$ fragment which comprises two antigen-binding domains and can crossreact with antigens, and the other is the remaining fragment (referred to as pFc'). Herein, an antibody fragment equivalent to that obtained by pepsin digestion is referred to as a "F(ab')$_2$-like antibody" when it comprises two antigen-binding domains and can crossreact with antigens. Such antibody fragments can also be produced, for example, by genetic engineering. Such antibody fragments can also be isolated, for example, from the antibody phage library described above. Alternatively, $F(ab')_2$-SH fragments can be recovered directly from hosts, such as *E. coli*, and then allowed to form $F(ab')_2$ fragments by chemical crosslinking (Carter et al., Bio/Technology 10:163-167 (1992)). In an alternative method, $F(ab')_2$ fragments can be isolated directly from a culture of recombinant hosts.

Furthermore, antibodies for use in the present invention may be multispecific antibodies. A multispecific antibody is an antibody that has specificity to at least two different kinds of antigens. Although such a molecule usually binds to two antigens (i.e., a bispecific antibody), the "multispecific antibody" herein encompasses antibodies with specificity to more than two antigens (e.g., three antigens). The multispecific antibody can be a full-length antibody or fragment thereof (e.g., $F(ab')_2$ bispecific antibody). A bispecific antibody can be prepared by crosslinking the heavy and light chains of two types of antibodies (HL pairs), or from bispecific-antibody-producing cells produced by fusing hybridomas that produce different monoclonal antibodies (Millstein et al., Nature 305:537-539 (1983)). Alternatively, a bispecific antibody can be prepared by genetic engineering. Specifically, the variable domain of an antibody with binding specificity is fused to the constant domain sequence of an immunoglobulin. The above-mentioned constant domain sequence preferably comprises at least a part of the hinge, CH2, and the CH3 regions of the heavy chain constant domain of the immunoglobulin. Preferably, the CH1 region of the heavy chain required for binding with the light chain is also included. A DNA encoding the immunoglobulin heavy chain fusion is inserted into an expression vector to transform an appropriate host organism. As necessary, a DNA encoding the immunoglobulin light chain is also inserted into an expression vector, different to that of the immunoglobulin heavy chain fusion, to transform the host organism. There are cases where the antibody yield increases when the chain ratio is not identical. In such cases, it is more convenient to insert each of the genes into separate vectors, since the expression ratio of each of the chains can be controlled. However, genes encoding a number of chains can also be inserted into one vector.

The term "diabody (Db)" refers to a bivalent antibody fragment constructed by gene fusion (for example, P. Holliger et al., Proc. Natl. Acad. Sci. USA 90: 6444-6448 (1993), EP 404,097, WO 93/11161). In general, a diabody is a dimer of two polypeptide chains. In the each of the polypeptide chains, a light chain variable region ($V_L$) and a heavy chain variable region ($V_H$) in an identical chain are connected via a short linker, for example, a linker of about five residues, so that they cannot bind together. Because the linker between the two is too short, the $V_L$ and $V_H$ in the same polypeptide chain cannot form a single chain V region fragment, but instead form a dimer. Thus, a diabody has two antigen-binding domains. When the $V_L$ and $V_H$ regions against the two types of antigens (a and b) are combined to form $V_L$a-$V_H$b and $V_L$b-$V_H$a via a linker of about five residues, and then co-expressed, they are secreted as bispecific Dbs. The antibodies of the present invention may be such Dbs.

A single-chain antibody (also referred to as "scFv") can be prepared by linking a heavy chain V region and a light chain V region of an antibody (for a review of scFv see Pluckthun "The Pharmacology of Monoclonal Antibodies" Vol. 113, eds. Rosenburg and Moore, Springer Verlag, N.Y., pp. 269-315 (1994)). Methods for preparing single-chain antibodies are known in the art (see, for example, U.S. Pat. Nos. 4,946,778, 5,260,203, 5,091,513, and 5,455,030). In such scFvs, the heavy chain V region and the light chain V region are linked together via a linker, preferably, a polypeptide linker (Huston, J. S. et al., Proc. Natl. Acad. Sci. U.S.A, 1988, 85, 5879-5883). The heavy chain V region and the light chain V region in a scFv may be derived from the same antibody, or from different antibodies. The peptide linker used to ligate the V regions may be any single-chain peptide consisting of 12 to 19 residues. A DNA encoding a scFv can be amplified by PCR using, as a template, either the entire DNA, or a partial DNA encoding a desired amino acid sequence, selected from a DNA encoding the heavy chain or the V region of the heavy chain of the above antibody, and a DNA encoding the light chain or the V region of the light chain of the above antibody; and using a primer pair that defines the two ends. Further amplification can be subsequently conducted using a combination of the DNA encoding the peptide linker portion, and the primer pair that defines both ends of the DNA to be ligated to the heavy and light chain respectively. After constructing DNAs encoding scFvs, conventional methods can be used to obtain expression vectors comprising these DNAs, and hosts transformed by these expression vectors. Furthermore, scFvs can be obtained according to conventional methods using the resulting hosts. These antibody fragments can be produced in hosts by obtaining genes that encode the antibody fragments and expressing these as outlined above. Antibodies bound to various types of molecules, such as polyethylene glycols (PEGs), may be used as modified antibodies. Methods for modifying antibodies are already established in the art. The term "antibody" in the present invention also encompasses the above-described antibodies.

The antibodies obtained can be purified to homogeneity. The antibodies can be isolated and purified by a method routinely used to isolate and purify proteins. The antibodies can be isolated and purified by the combined use of one or more methods appropriately selected from column chromatography, filtration, ultrafiltration, salting out, dialysis, preparative polyacrylamide gel electrophoresis, and isoelectro focusing, for example (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory, 1988). Such methods are not limited to those listed above. Chromatographic methods include affinity chromatography, ion exchange chromatography, hydrophobic chromatography, gel filtration, reverse-phase chromatography, and adsorption chromatography. These chromatographic methods can be practiced using liquid phase chromatography, such as HPLC and FPLC. Columns to be used in affinity chromatography include protein A columns and protein G columns. For example, protein A columns include Hyper D, POROS, and Sepharose F. F. (Pharmacia). Antibodies can also be purified by utilizing antigen binding, using carriers on which antigens have been immobilized.

The present invention provides suppressants for the inactivation of PC or aPC, which comprise the antibodies of the present invention. The present invention also relates to uses of the antibodies of the present invention in suppressing PC or aPC inactivation. The inactivation of PC or aPC in the presence of an aPC inhibitor, such as PCI or AAT, or the inactivation of PC or aPC in blood, can be suppressed by contacting an antibody of the present invention with PC or aPC. The present invention relates to methods for suppressing the inactivation of PC or aPC, which comprise a step of contacting an aPC antibody of the present invention with PC or aPC. An antibody of the present invention may be administered alone or in combination with PC and/or aPC. Furthermore, it is possible to administer PC or aPC which has been treated in vitro with an antibody of the present invention. In addition, the present invention provides methods for producing PC or aPC whose inactivation has been suppressed, where the methods comprise a step of allowing an antibody of the present invention to bind to PC or aPC. The present invention also provides the PC and aPC, whose inactivation has been suppressed, produced by these methods.

aPC is known to comprise the activities of suppressing blood coagulation and inflammation. Thus, the effect of aPC in suppressing blood coagulation or inflammation can be enhanced by the step of administering a non-neutralizing anti-aPC antibody of the present invention. The present invention relates to methods for suppressing blood coagulation or inflammation, which comprise the step of administering an antibody of the present invention. The methods may additionally comprise the step of administering PC and/or aPC. In this case, it is preferable to administer an antibody of the present invention which has been previously bound to PC and/or aPC. The therapeutic effect of aPC (e.g., the prevention and treatment of thrombosis and sepsis) can be enhanced by using a suppressant for aPC inactivation, which comprises an antibody of the present invention as an active ingredient. The phrase "comprises an antibody of the present invention as an active ingredient" means comprising an antibody of the present invention as at least one active ingredient, and does not indicate any limitation as to the content of the antibody of the present invention. The antibodies of the present invention are useful to prevent or treat diseases developed and/or advanced by a decrease or loss of activated protein C activity, and are particularly effective for preventing and/or treating diseases developed upon the enhancement of blood coagulation reaction and/or inflammatory reaction. Specific examples of such diseases include arterial thrombosis, venous thrombosis, disseminated intravascular coagulation (DIC) syndrome, and sepsis.

The present invention also provides kits which comprise: (a) an antibody of the present invention, and (b) PC and/or aPC. Such kits can be used to prevent or treat diseases developed and/or advanced upon a decrease or loss of activated protein C activity. In addition, the present invention provides kits for use in preventing or treating diseases developed and/or advanced upon a decrease or loss in activated protein C activity, which comprise: (a) at least one item selected from the group consisting of PC, aPC, and an antibody of the present invention, and (b) a recording medium comprising a description of the use of the antibody in combination with PC and/or aPC in therapeutically effective amounts, or a link to such a description. Such diseases include diseases developed upon the enhancement of the blood coagulation reaction and/or inflammatory reaction, as described above, and specifically include arterial thrombosis, venous thrombosis, DIC, and sepsis. The kits are useful to increase the relative in vivo activity of endogenous or administered PC or aPC. Thus, the kits can be used to prevent and treat the above-described diseases. The recording medium may be a desirable recording medium, including printable media, such as paper and plastic, floppy disk (FD), compact disk (CD), digital video disk (DVD), and computer-readable recording media, such as a semiconductor memory. These media are typically instruction manuals attached to a kit, which may contain a description of the combined use of the antibody and PC and/or aPC at therapeutically effective doses. A 'link' is defined as a connection with no direct description about the combined use of the antibody and PC and/or aPC at therapeutically effective doses, but that informs users of the location of the description via a label or such, allowing users to reach the description using the label. For example, an instruction manual that gives instructions or a suggestion to see an attached sheet, URL, or the like, which contains the description.

The antibodies of the present invention can be administered either orally or parenterally, but are preferably administered parenterally. Specific examples include injections, nasal formulations, pulmonary formulations, and cutaneous formulations. For example, injections can be administered systemically or locally by intravenous injection, intramuscular injection, intraperitoneal injection, or subcutaneous injection. Furthermore, the method of administration can be appropriately selected according to the age and symptoms of the patient. A single dose can be selected, from within the range of 0.0001 mg to 1,000 mg per kg of body weight. Alternatively, the dose can be selected, from within the range of 0.001 to 100,000 mg/body for each patient. However, the dose of an antibody of the present invention is not limited to these examples.

The antibodies of the present invention can be formulated according to standard methods (see, for example, Remington's Pharmaceutical Science, latest edition, Mark Publishing Company, Easton, U.S.A), and may comprise pharmaceutically acceptable carriers and/or additives. The present invention relates to compositions (including reagents and pharmaceuticals) comprising the antibodies of the invention, and pharmaceutically acceptable carriers and/or additives. Exemplary carriers include surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents.

However, the carriers that may be employed in the present invention are not limited to this list. In fact, other commonly used carriers can be appropriately employed: light anhydrous silicic acid, lactose, crystalline cellulose, mannitol, starch, carmelose calcium, carmelose sodium, hydroxypropylcellulose, hydroxypropylmethyl cellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on. The composition may also comprise other low-molecular-weight polypeptides, proteins such as serum albumin, gelatin, and immunoglobulin, and amino acids such as glycine, glutamine, asparagine, arginine, and lysine. When the composition is prepared as an aqueous solution for injection, it can comprise an isotonic solution comprising, for example, physiological saline, dextrose, and other adjuvants, including, for example, D-sorbitol, D-mannose, D-mannitol, and sodium chloride, which can also contain an appropriate solubilizing agent, for example, alcohol (for example, ethanol), polyalcohol (for example, propylene glycol and PEG), and non-ionic detergent (polysorbate 80 and HCO-50).

If necessary, antibodies of the present invention may be encapsulated in microcapsules (microcapsules made of hydroxycellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for making sustained-release drugs are known, and these can be applied for the antibodies of the present invention (Langer et al., J. Biomed. Mater. Res. 15: 167-277 (1981); Langer, Chem. Tech. 12: 98-105 (1982); U.S. Pat. No. 3,773,919; EP Patent Application No. 58,481; Sidman et al., Biopolymers 22: 547-556 (1983); EP: 133, 988).

In addition, genes encoding the antibodies of the present invention may be used for gene therapy, by cloning into vectors for such use. Such vectors can be administered by direct injection using naked plasmids, and also by packaging in liposomes, producing as a variety of viral vectors such as retroviral vectors, adenovirus vectors, vaccinia virus vectors, poxvirus vectors, adeno associated virus vectors, and HVJ vectors (Adolph, "Virus Genome Methods", CRC Press, Florida (1996)), or by coating onto carrier beads such as colloidal gold particles (for example, WO93/17706). However, any method can be used for administration, as long as the antibodies are expressed in vivo and exercise their function. Preferably, a sufficient dose may be administered by a suitable parenteral route (such as injecting intravenously, intraperitoneally, subcutaneously, percutaneously, or into adipose tissues or mammary glands, inhalation, intramuscular injection, infusion, gas-induced particle bombardment (using electron guns and such), or through mucosa, for example, using nose drops). Alternatively, genes encoding the antibodies of the present invention may be administered into cells ex vivo using liposome transfection, particle bombardment (U.S. Pat. No. 4,945,050), or viral infection, and the cells may be reintroduced into animals.

BRIEF DESCRIPTION OF THE DRAWINGS

FIG. 1 shows the amino acid sequences of the H chain and L chain variable regions of anti-aPC antibodies suppressing aPC inactivation. In this FIGURE, the amino acid sequences of the VH regions of aPC#79, aPC#123, aPC#281, and aPC#285 are respectively shown in SEQ ID NOs: 1 to 4. The amino acid sequences of the VL regions of aPC#79, aPC#123, aPC#281, and aPC#285 are respectively shown in SEQ ID NOs: 5 to 8.

BEST MODE FOR CARRYING OUT THE INVENTION

The present invention is illustrated in detail below with reference to Examples, but is not to be construed as being limited thereto. All publications cited herein are incorporated by reference in their entirety.

EXAMPLE 1

Preparation of Anti-Human aPC Monoclonal Antibodies

BALB/c mice were immunized by subcutaneous injection of aPC (Sigma P-2200) as an antigen into their abdominal areas. After elevation of the antibody titers in the sera was confirmed, the final immunization was carried out by injecting the antigen to the caudal vein at a dose of 20 µg/mouse. Three days after the final immunization, the spleen was excised and spleen cells were prepared. The cells were then fused with P3U1 cells. The fused cells were prepared in 2648 wells.

The day of fusion is defined as "Day 0". Using HAT medium, the culture medium was changed on Day 1, 2, 3, and 5, to select hybridomas using the HAT medium (which contained RPMI1640, 10% FCS, 0.1% penicillin-streptomycin, 2% BM-Condimed H1, and HAT). The culture supernatant was collected on Day 8, and the first screening was carried out using ELISA.

EXAMPLE 2

First Screening

The first screening was carried out with ELISA using aPC (SIGMA P-2200) as an antigen. After aPC was diluted to 0.5 µg/mL with a coating buffer (100 mmol/L NaHCO$_3$ (pH 9.6) and 0.02 w/v % NaN$_3$), 100 µL of the solution was aliquoted into each well of 96-well ELISA plates (Nunc, Maxisorp) and immobilized. The plates were washed with rinse buffer (PBS (−) and 0.05% Tween 20) using amicro plate washer (Bio-Rad, Model 1550). A 200-µL aliquot of the diluent buffer (1 w/v % BSA, 50 mmol/L Tris-HCl (pH 8.1), 150 mmol/L NaCl, 1 mmol/L MgCl$_2$, 0.05% Tween 20, and 0.02 w/v % NaN$_3$) was added to each well, and the plates were allowed to stand at room temperature for one hour. After the diluent buffer was removed, a 100-µL aliquot of culture supernatant of hybridomas was added to each well. The plates were incubated at room temperature for one hour. After the plates were washed with the rinse buffer, a 100-µL aliquot of a solution of alkaline phosphatase-conjugated anti-mouse IgG antibody (Zymed 62-6522) was added to each well. The plates were allowed to stand at room temperature for one hour. The plates were washed with rinse buffer, and then a 100-µL aliquot of 1 mg/mL substrate (p-nitrophenyl phosphate disodium; Sigma 104), prepared using the substrate buffer (50 mmol/L NaHCO$_3$ (pH 9.8) and 10 mmol/L MgCl$_2$), was added to each well. After one hour, OD405/655 nm was determined using a microplate reader (Bio-Rad Model 3550).

A commercially available anti-aPC antibody (SIGMA P7058), which binds to aPC, was used as a positive control. A culture supernatant was assessed to be positive when its absorbance was higher than that of the positive control at a concentration of 111 ng/mL. 308 positive wells were yielded upon screening of hybridoma culture supernatants from the 2648 wells.

EXAMPLE 3

Second Screening aPC has anticoagulant activity and thus extends blood plasma coagulation time. Longer incubation of aPC with blood plasma attenuates this effect because aPC is inactivated in blood plasma over time. If an antibody comprises the activity of suppressing aPC inactivation, the anticoagulant activity of aPC can be maintained by adding the antibody to aPC prior to incubation with blood plasma. Conversely, if the antibody is an aPC-neutralizing antibody, the anticoagulant activity of aPC will be lost. In this Example, hybridoma culture supernatants were tested for the activity of suppressing aPC inactivation. APTT (activated partial thromboplastin time) was used as an indicator of coagulation time.

10 μL of 10 μg/mL aPC (SIGMA, P-2200) solution was combined with 40 μL of hybridoma culture supernatant (cultured under an atmosphere of 5% $CO_2$ at 37° C. for three days) or P3U1 cell culture supernatant. The resulting mixture was incubated at room temperature for 60 minutes. 50 μL of human standard plasma (DADE BEHRING, GCH-100A) was added to the mixture, and then the resulting mixture was also incubated at room temperature for 60 minutes. The mixture was placed in an automatic analyzer for blood coagulation (Amelung, KC-10A), and 50 μL of APTT reagent (DADE BEHRING, GAA-200A) was added to the mixture. An aPC sample which had not been incubated with blood plasma was added to blood plasma immediately before addition of the APTT reagent. After incubation at 37° C. for three minutes, 50 μL of 20 mmol/L $CaCl_2$ (DADE BEHRING, GMZ-310) was added to the mixture, and then the time required for coagulation was determined.

The coagulation time-extending activity of hybridoma culture supernatants was determined based on the following formula: Inactivation suppression rate (%)={(C−B)/(A−B)}× 100, where A refers to the coagulation time when the above-described aPC incubated without blood plasma had been added, which is taken as 100%; B refers to the coagulation time when aPC incubated with blood plasma had been added, after incubation with P3U1 cell culture supernatant, which is taken as 0%; C refers to the coagulation time when aPC incubated with blood plasma had been added after incubation with hybridoma culture supernatant.

The experiments were carried out in duplicate (experiments 1 and 2). The supernatants were assessed as positive when they showed an improved coagulation time of 20% or higher in both experiments. The culture supernatants of 19 hybridoma lines were found to be positive.

TABLE 1

| WELL NUMBER | INACTIVATION SUPPRESSION RATE (%) | |
|---|---|---|
| | EXPERIMENT 1 | EXPERIMENT 2 |
| 19 | 36.83 | 20.48 |
| 41 | 46.81 | 55.49 |
| 50 | 23.74 | 21.14 |
| 64 | 45.70 | 32.02 |
| 79 | 87.96 | 68.33 |
| 123 | 23.45 | 20.68 |
| 143 | 25.27 | 34.10 |
| 172 | 25.52 | 58.64 |
| 181 | 26.22 | 33.66 |
| 192 | 21.36 | 30.18 |
| 223 | 26.87 | 22.92 |
| 236 | 24.56 | 21.66 |
| 240 | 22.18 | 22.19 |
| 243 | 21.25 | 27.87 |
| 263 | 21.00 | 27.96 |
| 281 | 33.82 | 21.64 |
| 285 | 24.50 | 28.23 |
| 298 | 32.29 | 27.19 |
| 302 | 27.30 | 20.75 |

EXAMPLE 4

Purification of Antibodies and Testing of Antibody Activity in Suppressing aPC Inactivation by PCI Hybridomas corresponding to well Nos. 19, 41, 64, 79, 281, and 298 were cultured in HAT medium comprising 10% ultra low IgG FCS. IgG fractions were purified from the culture supernatants using protein G columns, and PCI's activity in inactivating aPC was assessed using a low-molecular-weight substrate.

Specifically, the hybridomas were cultured in 50 mL of HAT medium containing 10% ultra low IgG FCS, and the culture supernatants were then collected. The culture supernatants were loaded onto protein G columns for adsorption (Amersham Pharmacia Biotech, HiTrap protein G column). After the columns were washed with 10 mL of Binding buffer (20 mmol/L phosphate buffer (pH 7.0)), elution was conducted with Elution buffer (0.1 mol/L glycine buffer (pH 2.7)). The IgG fractions collected were concentrated using Centriprep (Millipore, YM-30), and then the buffer was replaced with TBS buffer. 40 μL of the IgG fraction obtained was incubated with 10 μL of 10 μg/mL aPC solution at room temperature for 60 minutes. 50 μL of the aPC/antibody mixture was added to a buffer (final concentrations: 70 mmol/L Tris pH 8.0, 125 mmol/L NaCl, 10 mmol/L $CaCl_2$, and 0.1% BSA) containing 10 U heparin, and the volume of the mixture was adjusted to 180 μL. 20 μL of 100 μg/mL recombinant PCI (with Flag tag) was combined with the mixture, and then the resulting mixture was incubated at 37° C. for 30 minutes. 50 μL of the low-molecular-weight substrate S-2366 (2 mmol/L) was added to the mixture. After 60 minutes, the solution was assayed to determine its absorbance (at 405 nm).

TABLE 2

| | CONTROL | 19 | 41 | 64 | 79 | 281 | 298 | −PCI |
|---|---|---|---|---|---|---|---|---|
| | 0.278 | 0.303 | 0.325 | 0.304 | 0.357 | 0.345 | 0.270 | 0.690 |
| | 0.245 | 0.301 | 0.308 | 0.316 | 0.356 | 0.330 | 0.221 | 0.724 |
| AVERAGE | 0.262 | 0.302 | 0.317 | 0.310 | 0.357 | 0.338 | 0.246 | 0.707 |
| aPC ACTIVITY (%) | 0.00 | 9.09 | 12.35 | 10.89 | 21.32 | 17.06 | (−3.59) | 100.00 |

While the absorbance was 0.707 for aPC in the absence of PCI ("–PCI" in the Table), it decreased to 0.262 upon PCI addition ("control" in the Table). The relative activity of antibodies derived from each hybridoma was determined based on mean absorbance, where aPC activity in the presence of PCI was taken as 0%, and in the absence of PCI as 100%. The activity was 21% for well No. 79; 17% for well No. 281; and 12% for well No. 41. Thus, the antibodies suppressed aPC inactivation by PCI. The antibody of well No. 298 did not suppress aPC inactivation at all, and isotyping using the culture supernatant suggested it was IgM. Thus, it is possible that an active fraction would not be yielded in IgG purification. Based on the above-described chromogenic assay using the purified antibodies and the low-molecular-weight substrate, those antibodies suppressing aPC inactivation, which comprise the activity of extending blood plasma coagulation time, were also revealed to suppress inactivation by PCI.

EXAMPLE 5

Analysis of the H and L Chains of Anti-aPC Antibodies Suppressing aPC Inactivation Total RNA was extracted from about $1 \times 10^7$ cells of each antibody-producing hybridoma using Rneasy Plant Mini Kits (QIAGEN, Cat. No. 74904). Complementary DNA was synthesized from the total RNA using a SMART RACE cDNA Amplification Kit (Clontech, Cat. No. K1811-1). The H and L chains of #281 and #285 were PCR-amplified using primers specific to the IgG1 constant region, and the chains of #79 and #123 were PCR-amplified using primers specific to the IgG2b constant region. The 5'-RACE PCR experiments were carried out using an Advantage2 PCR Kit. The DNA fragments of the amplified H and L chains were cloned into pGEM-T easy vectors (Promega, Cat. No. A1360), and then sequenced.

The nucleotide sequences obtained were analyzed, and FIG. 1 shows the amino acid sequences of the H and L chain variable regions. #123 and #285 have similar sequences. The epitopes for these two clones were deduced to be closely located.

INDUSTRIAL APPLICABILITY

The present invention provides non-neutralizing anti-aPC antibodies that suppress aPC inactivation. The antibodies of the present invention comprise the activity of maintaining aPC activity by suppressing aPC inactivation, and thus comprise the activity of sustaining aPC bioactivities, such as the activity of suppressing the activation of the blood coagulation system, and anti-inflammatory activity. The antibodies of the present invention can be used to prevent or treat diseases or disorders developed and/or advanced upon a decrease or loss of the activity of activated protein C, and in particular the antibodies of the present invention are useful when using aPC for the prevention and treatment of diseases, such as thrombosis and sepsis.

---

The invention claimed is:

1. An antibody against protein C or activated protein C (aPC), comprising the heavy chain complementarity determining regions (CDRs) 1, 2, and 3 having the sequences of SEQ ID NOs: 9, 10, and 11, respectively; and light chain CDRs 1, 2, and 3 having the sequences of SEQ ID NOs: 21, 22, and 23, respectively.

2. The antibody of claim 1, wherein the antibody is selected from the group consisting of a chimeric antibody, antibody fragment, single-chain antibody, and diabody.

3. A composition comprising the antibody of claim 1 and a pharmaceutically acceptable carrier.

4. The antibody of claim 1, wherein the antibody is a human antibody or a humanized antibody.

5. An antibody that binds to the same epitope of protein C or aPC as an antibody comprising the CDR sequences of any of one of:
   (a) the heavy chain CDRs 1, 2, and 3 having the sequences of SEQ ID NOs: 9, 10, and 11, respectively; and light chain CDRs 1, 2, and 3 having the sequences of SEQ ID NOs: 21, 22, and 23, respectively;
   (b) heavy chain CDRs 1,2, and 3 having the sequences of SEQ ID NOs: 31, 32, and 33, respectively; and light chain CDRs 1, 2, and 3 having the sequences of SEQ ID NOs: 24, 25 and, 34, respectively; or
   (c) heavy chain CDRs 1, 2, and 3 having the sequences of SEQ ID NOs: 15, 16, and 17, respectively; and light chain CDRs 1, 2, and 3 having the sequences of SEQ ID NOs: 27, 28, and 29, respectively.

6. The antibody of claim 5, wherein the antibody is selected from the group consisting of a human antibody, humanized antibody, chimeric antibody, antibody fragment, single-chain antibody, and diabody.

7. A composition comprising the antibody of claim 5 and a pharmaceutically acceptable carrier.

8. An antibody against protein C or aPC comprising heavy chain CDRs 1, 2, and 3 having the sequences of SEQ ID NOs: 31, 32, and 33, respectively; and light chain CDRs 1, 2, and 3 having the sequences of SEQ ID NOs: 24, 25 and, 34, respectively.

9. The antibody of claim 8, wherein the antibody is a human antibody or a humanized antibody.

10. The antibody of claim 8, wherein the antibody is selected from the group consisting of a chimeric antibody, antibody fragment, single-chain antibody, and diabody.

11. A composition comprising the antibody of claim 8 and a pharmaceutically acceptable carrier.

12. An antibody against protein C or aPC comprising heavy chain CDRs 1, 2, and 3 having the sequences of SEQ ID NOs: 15, 16, and 17, respectively; and light chain CDRs 1, 2, and 3 having the sequences of SEQ ID NOs: 27, 28, and 29, respectively.

13. The antibody of claim 12, wherein the antibody is a human antibody or a humanized antibody.

14. The antibody of claim 12, wherein the antibody is selected from the group consisting of a chimeric antibody, antibody fragment, single-chain antibody, and diabody.

15. A composition comprising the antibody of claim 12 and a pharmaceutically acceptable carrier.

* * * * *

UNITED STATES PATENT AND TRADEMARK OFFICE
CERTIFICATE OF CORRECTION

PATENT NO.       : 7,517,965 B2                                    Page 1 of 1
APPLICATION NO.  : 10/522086
DATED            : April 14, 2009
INVENTOR(S)      : Takaki Koga et al.

It is certified that error appears in the above-identified patent and that said Letters Patent is hereby corrected as shown below:

On the title page,

[*] Notice:   Subject to any disclaimer, the term of this patent is extended or adjusted under 35 USC 154(b) by (268) days Delete the phrase "by 268 days" and insert -- by 356 days --

Signed and Sealed this

Twenty-fourth Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,517,965 B2  
APPLICATION NO. : 10/522086  
DATED : April 14, 2009  
INVENTOR(S) : Koga et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 714 days.

Signed and Sealed this
Twenty-sixth Day of July, 2011

David J. Kappos  
*Director of the United States Patent and Trademark Office*